United States Patent
Sugiura et al.

(10) Patent No.: US 11,141,708 B2
(45) Date of Patent: Oct. 12, 2021

(54) CELL CULTURE APPARATUS AND CELL CULTURE METHOD

(71) Applicant: NATIONAL INSTITUTE OF ADVANCED INDUSTRIAL SCIENCE AND TECHNOLOGY, Tokyo (JP)

(72) Inventors: Shinji Sugiura, Tsukuba (JP); Taku Satoh, Tsukuba (JP); Toshiyuki Kanamori, Tsukuba (JP); Kazumi Shin, Tsukuba (JP)

(73) Assignee: NATIONAL INSTITUTE OF ADVANCED INDUSTRIAL SCIENCE AND TECHNOLOGY

( * ) Notice: Subject to any disclaimer, the term of this patent is extended or adjusted under 35 U.S.C. 154(b) by 387 days.

(21) Appl. No.: 15/562,447

(22) PCT Filed: Mar. 8, 2016

(86) PCT No.: PCT/JP2016/057107
§ 371 (c)(1),
(2) Date: Sep. 28, 2017

(87) PCT Pub. No.: WO2016/158233
PCT Pub. Date: Oct. 6, 2016

(65) Prior Publication Data
US 2018/0085726 A1    Mar. 29, 2018

(30) Foreign Application Priority Data

Apr. 3, 2015 (JP) .............................. JP2015-077196

(51) Int. Cl.
*C12M 1/00* (2006.01)
*C12M 1/04* (2006.01)
(Continued)

(52) U.S. Cl.
CPC ....... *B01J 19/0046* (2013.01); *B01F 13/0059* (2013.01); *B01L 3/502* (2013.01);
(Continued)

(58) Field of Classification Search
CPC ................. B01F 13/0059; B01L 3/502; B01L 3/502738; B01L 2200/0621;
(Continued)

(56) References Cited

U.S. PATENT DOCUMENTS

2003/0044324 A1* 3/2003 Micklash, II ........... B01L 9/523
422/504
2008/0130402 A1   6/2008 Karaki et al.
(Continued)

FOREIGN PATENT DOCUMENTS

CN          1326549 A      12/2001
CN        100531915 C       8/2009
(Continued)

OTHER PUBLICATIONS

International Search Report dated May 24, 2016 in corresponding PCT International Application No. PCT/JP2016/057107.
(Continued)

*Primary Examiner* — Liban M Hassan
(74) *Attorney, Agent, or Firm* — Ostrolenk Faber LLP

(57) ABSTRACT

A cell culture apparatus, includes a connected culture container including n number of units disposed in parallel along a second direction that is a different direction from a first direction where each of the n number of the units is constituted of m number of culture chambers and one or more communication-channels, the m number of the culture chambers each having a cell-holding portion that holds seeded cells, the m number of the culture chambers storing liquid culture media, the m number of the culture chambers being disposed in parallel along the first direction, the
(Continued)

communication-channels communicating the m number of the culture chambers with each other; and a plurality of pneumatic pipes communicating same-row-disposed culture chambers that are disposed on a same row along the second direction with each other in the connected culture container.

9 Claims, 27 Drawing Sheets

(51) Int. Cl.
  *C12M 1/12* (2006.01)
  *C12M 1/36* (2006.01)
  *B01J 19/00* (2006.01)
  *B01L 3/00* (2006.01)
  *C12M 3/06* (2006.01)
  *B01F 13/00* (2006.01)

(52) U.S. Cl.
  CPC ....... *B01L 3/502738* (2013.01); *C12M 1/005* (2013.01); *C12M 1/04* (2013.01); *C12M 1/12* (2013.01); *C12M 1/36* (2013.01); *C12M 23/04* (2013.01); *C12M 23/16* (2013.01); *C12M 29/10* (2013.01); *C12M 29/14* (2013.01); *B01L 2200/0621* (2013.01); *B01L 2300/088* (2013.01); *B01L 2300/0829* (2013.01); *B01L 2300/0874* (2013.01); *B01L 2400/0487* (2013.01); *B01L 2400/0688* (2013.01)

(58) Field of Classification Search
  CPC ....... B01L 2300/088; B01L 2300/0874; B01L 2300/0829; B01L 2400/0688; B01L 2400/0487; B01J 19/0046; C12M 1/005; C12M 1/04; C12M 1/12; C12M 1/36; C12M 23/04; C12M 23/16; C12M 29/10; C12M 29/14
  USPC .......................................... 435/286.1, 289.1
  See application file for complete search history.

(56) References Cited

U.S. PATENT DOCUMENTS

| | | | |
|---|---|---|---|
| 2008/0153152 | A1 | 6/2008 | Wakabayashi et al. |
| 2011/0039285 | A1* | 2/2011 | Sadaba Champetier De Ribes .... B01L 3/5027 435/13 |
| 2012/0214189 | A1* | 8/2012 | Shuler .................... C12M 23/16 435/29 |
| 2013/0143218 | A1* | 6/2013 | Brown .................. B01L 3/5027 435/6.11 |

FOREIGN PATENT DOCUMENTS

| | | | |
|---|---|---|---|
| CN | 101868723 | A | 10/2010 |
| CN | 102257124 | A | 11/2011 |
| JP | 2009-527225 | A | 7/2009 |
| JP | 2011-257238 | A | 12/2011 |
| JP | 2015-073468 | A | 4/2015 |
| KR | 10-2014-0008629 | A | 1/2014 |
| KR | 101404657 | B1 | 6/2014 |
| WO | WO 2007/098027 | A2 | 8/2007 |
| WO | WO 2013/086329 | A1 | 6/2013 |
| WO | WO 2013/086486 | A1 | 6/2013 |

OTHER PUBLICATIONS

Written Opinion dated May 24, 2016 in corresponding PCT International Application No. PCT/JP2016/057107.
F. Pammolli et al., Nat. Rev. Drug Discov, 10, 428-438 (2011).
S.N. Bhatia et al., Nat. Biotechnol., 32, 760-772 (2014).
C.Y. Chan et al., Lab Chip,13, 4697-4710 (2013).
J.H. Sung et al., Lab Chip, 10, 446-455 (2010).
I. Wagner et al., Lab Chip, 13, 3538-3547 (2013).
J.H. Sung et al., Lab Chip, 13, 1201-1212 (2013).
S. Sugiura et al., Anal. Chem., 82, 8278-8282 (2010).
S. Sugiura et al., Biotechnol. Bioeng., 100, 1156-1165 (2008).
K. Hattori et al., J. Biosci. Bioeng., 118, 327-332 (2014).
C. Zhang, et al., Lab Chip, 9, 3185-3192 (2009).
Office Action dated Aug. 27, 2020, issued in corresponding Chinese Patent Application No. 201680019753.4. English translation of Search Report. Total 12 pages.

* cited by examiner

CELL CULTURE APPARATUS AND CELL CULTURE METHOD

CROSS-REFERENCE TO RELATED APPLICATIONS

The present application is a 35 U.S.C. §§ 371 national phase conversion of PCT/JP2016/057107, filed Mar. 8, 2016, which claims priority to Japanese Patent Application No. 2015-077196, filed Apr. 3, 2015, the contents of which are incorporated herein by reference. The PCT International Application was published in the Japanese language.

TECHNICAL FIELD

The present invention relates to a cell culture apparatus and a cell culture method which relate to analysis techniques for medicinal products or chemical products and are intended to analyze the medicinal effects or toxicity of medicinal products or chemical products and pharmacokinetics such as absorption, distribution, metabolism, and excretion using cultured cells.

BACKGROUND ART

In recent years, medicinal product development costs have significantly increased, and, according to Non-Patent Document 1 announced by Pammolli in 2011, a significant increase of the probability of the dropout of medicinal product candidate compounds in phase II and phase III clinical trials is pointed out as one of significant causes. Although there are arguments regarding the causes for a decrease in development success percentages, in order to prevent the dropout in clinical trials of candidate compounds that are considered to be promising in preclinical trials, it is important to obtain in preclinical trial stages data having a favorable correlation with clinical trials.

In preclinical trials, tests for evaluating medicinal effects, medicinal kinetics, and toxicity using cultured cells are often used. In tests in which cultured cells are used, a significant difference between culturing environments and environments inside living organisms is considered as a cause for poor correlations with clinical trials. In addition, even when medicinal effects, medicinal kinetics, and toxicity are evaluated using one type of cultured cells, it is difficult to evaluate phenomena relating to a plurality of organs in living organisms, and this difficulty is considered as one of the causes for poor correlations between tests in which cultured cells are used and clinical trials. In animal bioassay, a difference in biotic functions attributed to a difference in species is considered as a significant cause for poor correlations with test results.

A Body-on-a-chip system is a method in which cultured cells are used as organ models, and a plurality of organ models are connected to each other and cultured, thereby reconstituting phenomena in living organisms relating to a plurality of organs outside living organisms. The Body-on-a-chip system holds a potentiality as an alternative animal bioassay in which medicinal kinetic analyses that generally require animal bioassay can be carried out in vitro and has rapidly attracted attention in recent years (refer to Non-Patent Document 2 and Non-Patent Document 3). Particularly, when medicinal kinetic analyses can be evaluated in vitro using cultured cells originated from human beings, it is expected that data having a favorable correlation with clinical trials can be acquired.

However, a majority of these studies still remain as principle verification studies that evaluate model compounds which can be easily verified using two or three types of organ models (Non-Patent Documents 4 to 6), and the evaluation of the correlation between the Body-on-a-chip system and animal bioassay and clinical trials has not yet been finalized. In order to clarify this vivo/vitro correlation, it is necessary to verify the effectiveness of the Body-on-a-chip system using a variety of organ models or model compounds. Furthermore, in order to use the Body-on-a-chip system for drug development as an alternative animal bioassay, high-throughput screening that evaluates multiple types of compounds at the same time is necessary, which still remains unsolved in the above-described principle verification studies.

The present inventors and the like have already developed a "pressure-driven perfusion culture microchamber array" in which a number of medicinal solutions can be conveniently handled (refer to Non-Patent Document 7 and Non-Patent Document 8) in the previous studies, then, developed a circulation culturing system including a platform having favorable usability, and carried out user evaluation for putting this system into practical use (refer to Non-Patent Document 9 and Patent Document 1).

PRIOR ART DOCUMENTS

Patent Documents

[Patent Document 1] Japanese Unexamined Patent Application, First Publication No. 2015-73468

Non-Patent Documents

[Non-Patent Document 1] F. Pammolli, et al., Nat. Rev. Drug Discov, 10, 428 (2011)
[Non-Patent Document 2] S. N. Bhatia and D. E. Ingber, Nat. Biotechnol., 32, 760 (2014)
[Non-Patent Document 3] C. Y. Chan, et al., Lab Chip, 13, 4697 (2013)
[Non-Patent Document 4] J. H. Sung, et al., Lab Chip, 10, 446 (2010)
[Non-Patent Document 5] I. Wagner, et al., Lab Chip, 13, 3538 (2013)
[Non-Patent Document 6] J. H. Sung, et al., Lab Chip, 13, 1201 (2013)
[Non-Patent Document 7] S. Sugiura, et al., Anal. Chem., 82, 8278 (2010)
[Non-Patent Document 8] S. Sugiura, et al., Biotechnol. Bioeng., 100, 1156 (2008)
[Non-Patent Document 9] K. Hattori, et al., J. Biosci. Bioeng., 118, 327 (2014)
[Non-Patent Document 10] C. Zhang, et al., Lab Chip, 9, 3185 (2009)

SUMMARY OF THE INVENTION

Problems to be Solved by the Invention

In order to use the Body-on-a-chip system for drug development as an alternative animal bioassay, high-throughput screening that evaluates multiple types of compounds at the same time is necessary, but this necessity has not yet been realized at the moment.

Therefore, an object of the present invention is to develop a "pressure-driven Body-on-a-chip system" in which high-throughput screening that evaluates multiple types of compounds at the same time can be realized by further advancing a "pressure-driven perfusion culture microchamber array" according to the relevant knowledge that has been previously accumulated by the present inventors and the like and to enable evaluations in which a variety of organ-connecting models and model compounds are used.

Means for Solving the Problems

In order to achieve the above-described object, a cell culture apparatus according to one aspect of the present invention is a cell culture apparatus in which culture chambers are connected to each other using microchannels, pressure pipe lines distributing pressure are connected to each of the culture chambers, and multiple types of compounds can be evaluated at the same time by sending liquid culture media in a variety of the culture chambers at the same time by means of pressure driving.

The cell culture apparatus according to a first aspect of the present invention includes a connected culture container including n number of units disposed in parallel along a second direction that is a different direction from a first direction where each of the n number of the units is constituted of m number of culture chambers and one or more communication-channels, the m number of the culture chambers each having a cell-holding portion that holds seeded cells, the m number of the culture chambers storing liquid culture media, the m number of the culture chambers being disposed in parallel along the first direction, the communication-channels communicating the m number of the culture chambers with each other; and a plurality of pneumatic pipes communicating same-row-disposed culture chambers that are disposed on a same row along the second direction with each other in the connected culture container, the pneumatic pipes being configured to pressurize the same-row-disposed culture chambers at the same time or open the same-row-disposed culture chambers to atmospheric pressure at the same time, the pneumatic pipes being configured to send the liquid culture media to the m number of the culture chambers through the communication-channels using pressure differences in the m number of the culture chambers, in which m is an integer of two or more, and n is an integer of two or more.

A backward flow prevention mechanism configured to control flow directions from the communication-channels toward the m number of the culture chambers may be provided. The backward flow prevention mechanism may be provided at an end of the communication-channels or in the communication-channels.

Each of the m number of the culture chambers may include a container-shaped tank main body storing liquid culture media and a lid portion configured to open an opening of the tank main body or air-tightly close the opening.

A lid portion-pressing portion configured to hold the lid portion so as to be pressed toward the tank main body may be provided. The lid portion-pressing portion may include a base body portion that supports the tank main body and a pressing member that presses the lid portion toward the tank main body supported by the base body portion.

The tank main body may include a wall portion and a bottom plate including the communication-channels.

A wall portion-pressing portion that holds the wall portion so as to be pressed toward the bottom plate may be provided. The wall portion-pressing portion may include a pressing member that presses the wall portion toward the base body portion and the bottom plate supported by the base body portion.

Pressurizing apparatuses configured to sequentially pressurize each of the culture chambers or open each of the culture chambers to atmospheric pressure through the pneumatic pipes according to preset schedules in each of the culture chambers may be provided.

A Laplace valve configured to prevent flows of air using interface tension at portions connected to the communication-channels from the culture chambers may be provided. When a width of a microchannel constituting the Laplace valve is represented by $w_L$, a depth of the microchannel is represented by $h_L$, the interface tension is represented by $\gamma$, and a Laplace pressure of the Laplace valve is represented by $\Delta P_{Lap}$, the Laplace pressure is expressed by an expression of $\Delta P_{Lap} = 2\gamma(1/w_L + 1/h_L)$, and the microchannel may be constituted so that the Laplace pressure $\Delta P_{Lap}$ becomes larger than a pressure applied to the connected culture container.

A resistance channel portion having a channel cross-sectional area that is 1/10 or less of a channel cross-sectional area of a communication-channel may be provided in a part of the communication-channels in order to adjust flow rates.

The backward flow prevention mechanisms may be a check valve.

The backward flow prevention mechanism may be the backward flow prevention-Laplace valve.

A cell culture method according to a second aspect of the present invention includes preparing a cell culture apparatus in which, m number of culture chambers communicate with each other using one or more communication-channels, n number of units of a connected culture container in which the m number of the culture chambers are disposed in parallel along a first direction are provided, and the n number of the units of the connected culture container are disposed in parallel along a second direction that is a different direction from the first direction; a first step of opening a lid of the connected culture container and seeding and adhering cells in each of the culture chambers in the cell culture apparatus; a second step of filling first row-culture chambers in the first direction with a liquid culture medium and closing the lid in the cell culture apparatus where the first row-culture chambers are disposed on a same row along the second direction; a third step of pressurizing an inside of the first row-culture chambers and opening second row-culture chambers in the first direction which are disposed on a same row along the second direction to atmospheric pressure, thereby sending the liquid culture medium to the second row-culture chambers from the first row-culture chambers through the communication-channels; a fourth step of sequentially pressurizing the culture chambers and opening the culture chambers to atmospheric pressure in ascending order of row numbers in the first direction, thereby sending the liquid culture medium from the m−1$^{th}$ row-culture chambers in the first direction to the m$^{th}$ row-culture chambers through the communication-channels; a fifth step of pressurizing an inside of the m$^{th}$ row-culture chambers and opening an inside of the first row-culture chambers to atmospheric pressure, thereby sending the liquid culture medium from the m$^{th}$ row-culture chambers to the first row-culture chambers through the communication-channels; and a sixth step of repeating the third step through the fifth step, thereby circulating the liquid culture medium in each of the culture chambers in the cell culture apparatus, in which m is an integer of two or more, and n is an integer of two or more.

An evaluation system according to a third aspect of the present invention may include cells introduced into the cell culture apparatus according to the above-described aspect.

Another aspect of the present invention is a cell culture apparatus including m number of culture chambers for storing liquid culture media, the respective culture chambers having cell-holding portions for holding seeded cells and, furthermore, n units of a connected culture container constituted by communicating the m number of the culture chambers through one or a plurality of communication-channels, in which m and n are integers of two or more, pneumatic pipes communicating the culture chambers on the same location in the respective units of the connected culture container with each other are provided, the culture chambers on the same location in the respective units of the connected culture container are pressurized at the same time or are opened to atmospheric pressure at the same time by pressurizing the culture chambers or opening the culture chambers to atmospheric pressure using the pneumatic pipes, and the liquid culture media are sent through the communication-channels using pressure differences in the culture chambers.

In addition, still another aspect of the present invention is the cell culture apparatus including check valves that control the flow directions from the communication-channels toward the culture chambers, the check valves being provided at terminals of the communication-channels or in the communication-channels.

In addition, still another aspect of the present invention is the cell culture apparatus, in which the culture chambers each have a container-shaped tank main body storing liquid culture media and a lid portion capable of opening/closing or air-tightly sealing an opening of the tank main body.

In addition, still another aspect of the present invention is the cell culture apparatus further including a lid portion-pressing portion holding the lid portion by pressing the lid portion toward the tank main body, in which the lid portion-pressing portion has a base body portion that supports the tank main body and a pressing member that presses the lid portion toward the tank main body supported by the base body portion.

In addition, still another aspect of the present invention is the cell culture apparatus, in which the tank main body has a wall portion and a bottom plate including communication-channels.

In addition, still another aspect of the present invention is the cell culture apparatus further including a wall portion-pressing portion that holds the wall portion by pressing the wall portion toward the bottom plate, in which the wall portion-pressing portion has the base body portion and a pressing member that presses the wall portion toward the bottom plate supported by the base body portion.

In addition, still another aspect of the present invention is the cell culture apparatus including pressurizing apparatuses that sequentially pressurize the respective culture chambers or open the respective culture chambers to atmospheric pressure through the pneumatic pipes according to preset schedules.

In addition, still another aspect of the present invention is the cell culture apparatus including Laplace valves that prevent the flows of air using interface tension at portions connected to the communication-channels from the culture chambers.

In addition, still another aspect of the present invention is the cell culture apparatus including resistance channel portions having a channel cross-sectional area of $1/10$ or less in parts of the communication-channels in order to adjust flow rates.

In addition, still another aspect of the present invention is a cell culture method in which a cell culture apparatus including m number of culture chambers and, furthermore, n number of units of a connected culture container constituted by communicating the m number of the culture chambers with each other through one or a plurality of communication-channels is used, and m and n are integers of two or more, including:

a step 1 of opening a lid of the connected culture container and seeding and adhering cells in the respective culture chambers in the respective units of the connected culture container, a step 2 of filling the culture chambers at a first location in the respective units with a liquid culture medium and closing the lid, a step 3 of pressurizing an inside of the culture chambers at the first location in the respective units and opening the culture chambers at a second location to atmospheric pressure, thereby sending the liquid culture medium to the culture chambers at the second location from the culture chambers at the first location through the communication-channels, a step 4 of sequentially pressurizing the culture chambers and opening the culture chambers to atmospheric pressure in ascending order of the location numbers, thereby sending the liquid culture medium from the culture chambers at an $m-1^{th}$ location to the culture chambers at an $m^{th}$ location through the communication channels, a step 5 of pressurizing an inside of the culture chambers at the $m^{th}$ location in the respective units and opening an inside of the culture chambers at the first location to atmospheric pressure, thereby sending the liquid culture medium from the culture chambers at the $m^{th}$ location to the culture chambers at the first location through the communication-channels, and a step 6 of repeating the step 3 through the step 5, thereby circulating the liquid culture medium in the m number of culture chambers in the respective units.

Effects of Invention

For example, in Non-Patent Documents 3 to 5, methods in which the force of gravity is used by inclining containers and methods in which liquid is sent using a device equipped with a peristaltic pump or an external syringe pump are employed; however, in these methods, apparatuses become complicated, and thus it is difficult to evaluate a number of compounds at the same time. In addition, in Non-Patent Documents 3 and 5, only one type of compound can be evaluated, and, in Non-Patent Document 4, only two types of compounds can be evaluated.

However, in the Body-on-a-chip system according to the present invention, which is obtained by further advancing the pressure-driven perfusion culture system of Patent Document 1 that has been previously applied by the present inventors and the like, it is possible to evaluate the effects of a number of medicines using a plurality of organ connecting models.

EMBODIMENTS FOR CARRYING OUT THE INVENTION

Figure 1A:
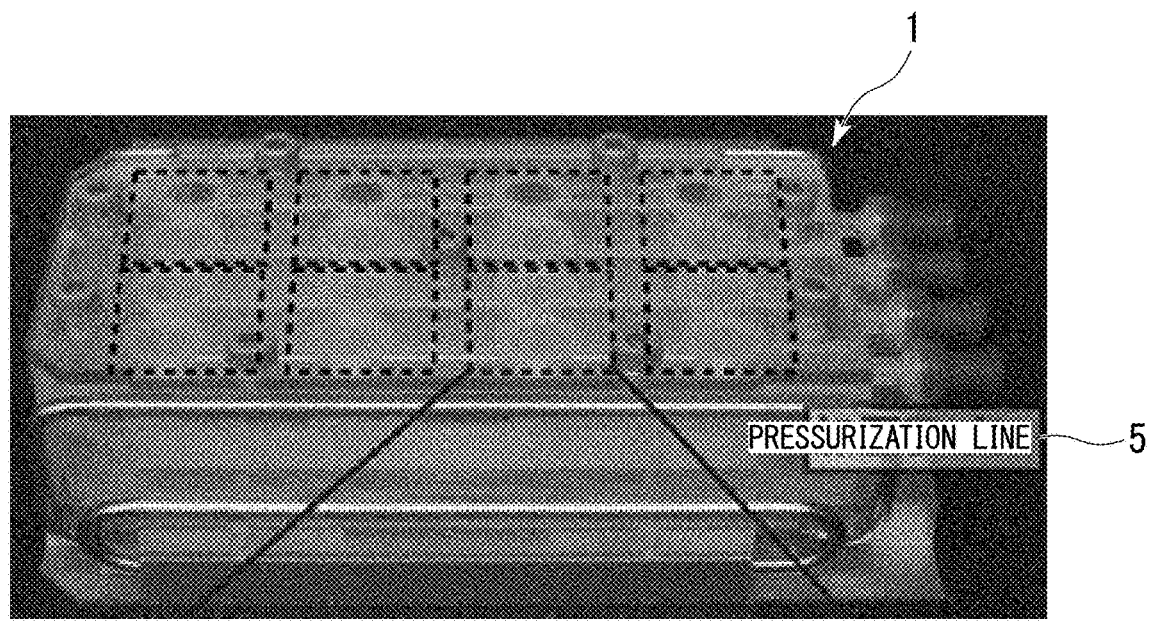
FIG. 1A is one production example of a pressure-driven cell culture apparatus according to a first embodiment of the present invention.
Figure 1B:
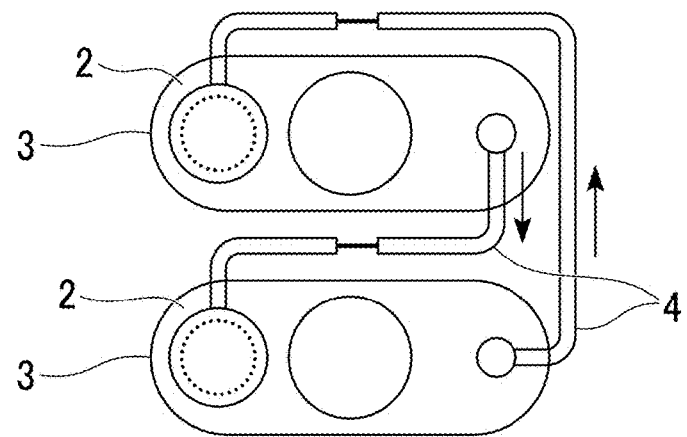
FIG. 1B is an enlarged view of two-connected-culture-chambers (Body-on-a-Chip unit) in the production example of the pressure-driven cell culture apparatus according to the first embodiment of the present invention.

A cell culture apparatus (Body-on-a-Chip unit) 1 according to a first embodiment of the present invention will be described using a system that evaluates eight types of compounds shown in FIGS. 1A and 1B using a connecting model of two types of organs as an example. The example of FIGS. 1A and 1B is constituted of a total of eight units in which two-connected-culture-chambers (two-organ connecting model) 3A in which two culture chambers 2 are connected to each other and thus form an organ model as shown in FIG. 1B is considered as one unit. The culture chambers 2 constituting one unit are connected to each other through microchannels 4. Culture fluids can be circulated in the respective organ model culture chambers 2 by sequentially pressurizing the chambers using pneumatic pipes (pressurization lines) 5 connected to the right side of FIG. 1A.

Figure 2A:
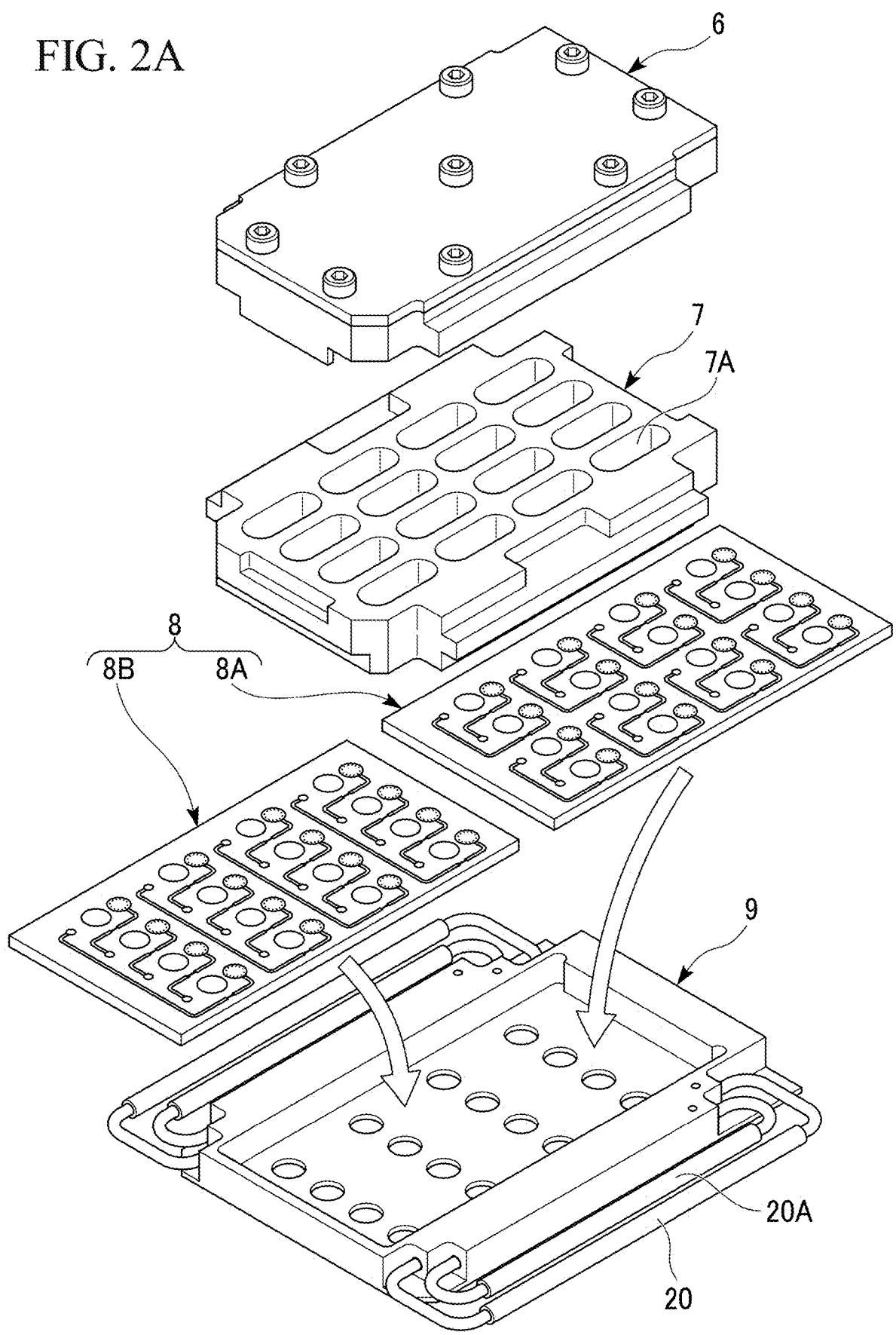
FIG. 2A is an overall constitutional view of an example of the pressure-driven cell culture apparatus according to the first embodiment of the present invention.

FIG. 2A is an overall constitutional view of a cell culture apparatus 1 according to the present embodiment which shows the system in FIGS. 1A and 1B in more detail, and the cell culture apparatus is constituted of four parts of a lid (pressurizing lid) 6, a through-hole plate (a plate having through-hole) 7, a microchannel plate 8, and a holder (base body portion) 9. This constitution can be applied to a variety of organ connecting models by designing the microchannel plate (bottom plate) 8 depending on designs such as the number of organs or the flow rates of culture media. In the example of FIG. 2A, it is also possible to use a microchannel plate 8A on which eight units of the two-organ connecting models 3A are mounted or a microchannel plate 8B on which four units of four-organ connecting models 3B are mounted. The cell culture apparatus 1 according to the present embodiment has a constitution in which a variety of organ connecting models can be operated by replacing the microchannel plate 8.

The system of FIG. 2A is constituted by overlaying the respective parts of the lid 6, the through-hole plate 7, the microchannel plate 8, and the holder (base body portion) 9. The respective parts will be described below in detail. The lid 6 is connected to holes processed on the side surface (not shown in FIG. 2; refer to introduction holes of pneumatic pipes 5 and 5A to 5D in FIGS. 12A to 12C) and distributes pressure introduced through the pneumatic pipes 5 to the respective culture chambers 2. The through-hole plate 7 constitutes wall surfaces (wall portions) 7A of the culture chambers 2.

The holder 9 fixes the lid 6, the through-hole plate 7, and the microchannel plate 8. In this case, when a flexible component such as a silicone rein sheet or an O ring (sealing material 21) is disposed between the lid 6 and the through-hole plate 7, it is possible to prevent pressure leakage through a gap between the lid 6 and the through-hole plate 7. In addition, when a flexible component such as a silicone resin is used as the microchannel plate 8, it is possible to prevent pressure leakage and liquid leakage through a gap between the microchannel plate 8 and the through-hole plate 7 and a gap between the microchannel plate 8 and the holder 9. In addition, in order to circulate culture fluids, it is also possible to install a check valve 11 in the through-hole plate 7. In the two-organ connecting model 3A, the installment of the check valve 11 is not essential.

Note that FIG. 2A shows an example in which the through-hole plate 7, the microchannel plate 8, and the holder 9 are separately formed.

The through-hole plate 7, the microchannel plate 8, and the holder 9 may be separately formed as shown in FIGS. 2A and 12A to 12C, or the through-hole plate 7, the microchannel plate 8, and the holder 9 may be integrally formed as shown in FIGS. 9A to 9E and 10A to 10G.

Note that, in FIGS. 9A to 9E, a member in which the through-hole plate 7, the microchannel plate 8, and the holder 9 are integrally formed is shown as a main body (tank main body) 1A, and, in FIGS. 10A to 10G, a member in which the through-hole plate 7, the microchannel plate 8, and the holder 9 are integrally formed is shown as a main body (tank main body) 101A.

Figure 2B:
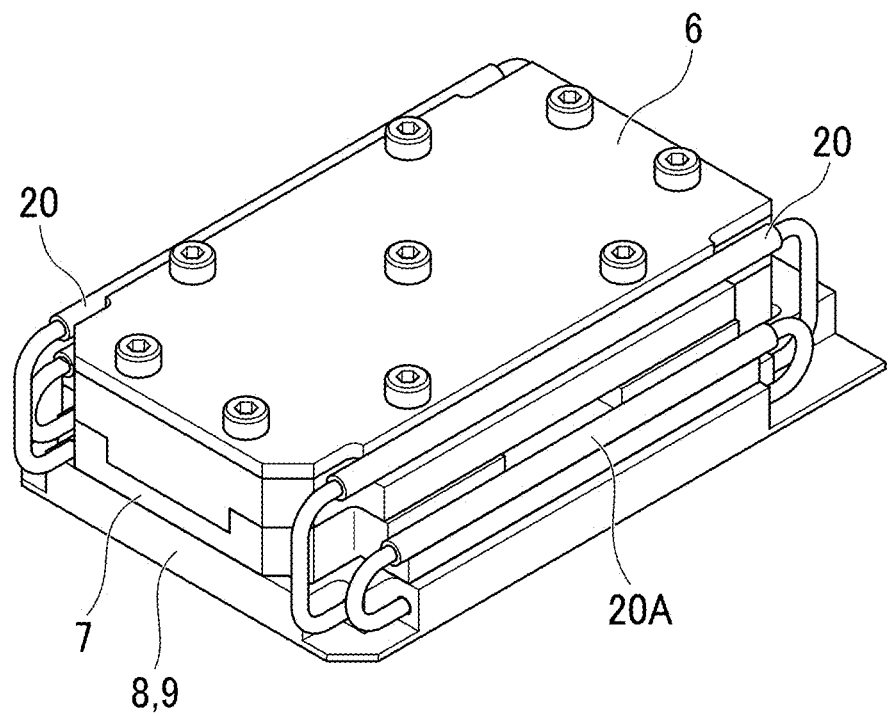
FIG. 2B is an overall constitution view of the example of the pressure-driven cell culture apparatus according to the first embodiment of the present invention (a perspective view of the assembled culture apparatus).

FIG. 2B is a perspective view of an assembled culture apparatus in a state in which the lid 6, the through-hole plate 7, the microchannel plate 8, and the holder 9 which are shown in FIG. 2A are assembled together.

Figure 2C:
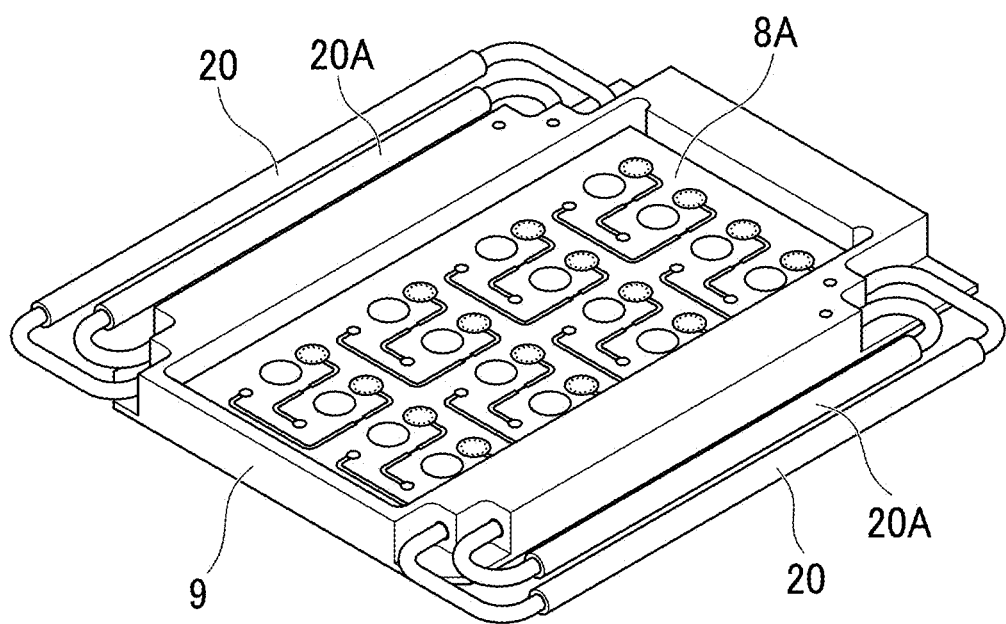
FIG. 2C is a perspective view showing a state in which a microchannel plate (bottom plate) is stored in a holder in the pressure-driven cell culture apparatus according to the first embodiment of the present invention.

FIG. 2C is a perspective view showing an example of a state in which the microchannel plate 8A is stored in the holder 9.

As shown in FIG. 2C, for example, the microchannel plate 8A is stored in the holder 9, and furthermore, the through-hole plate 7 is placed on the microchannel plate 8A stored in the holder 9. As shown in FIG. 2B, it is possible to attach the lid 6 to the through-hole plate 7 and fix the lid 6 using a first clasp 20. In this case, the lid 6 can be held using the first clasp 20 (lid portion-pressing portion or pressing member) so as to be pressed toward the tank main body 1A.

In addition, as shown in FIG. 2B, the through-hole plate 7 can be held using a second clasp 20A (wall portion-pressing portion or pressing member) so as to be pressed toward the microchannel plate (bottom plate) 8.

Figure 3:
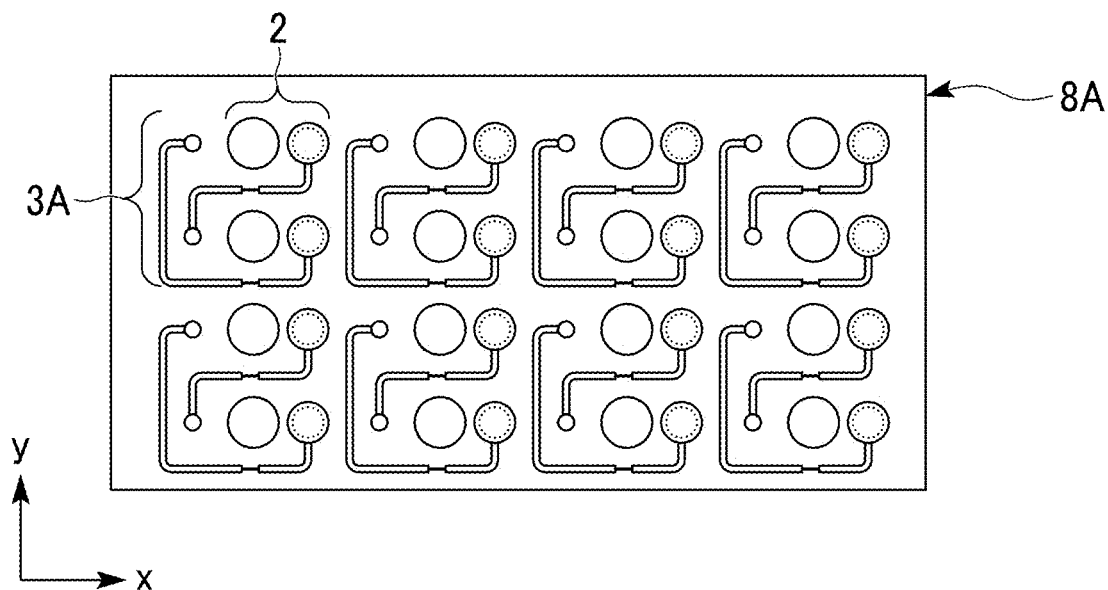
FIG. 3 is a channel constitution view (top view) of the microchannel plate in the pressure-driven cell culture apparatus shown in FIG. 2A and an example of a microchannel plate for a two-connected-culture-chamber-type eight-unit system (two-organ×eight-chamber connected plate).
Figure 4:
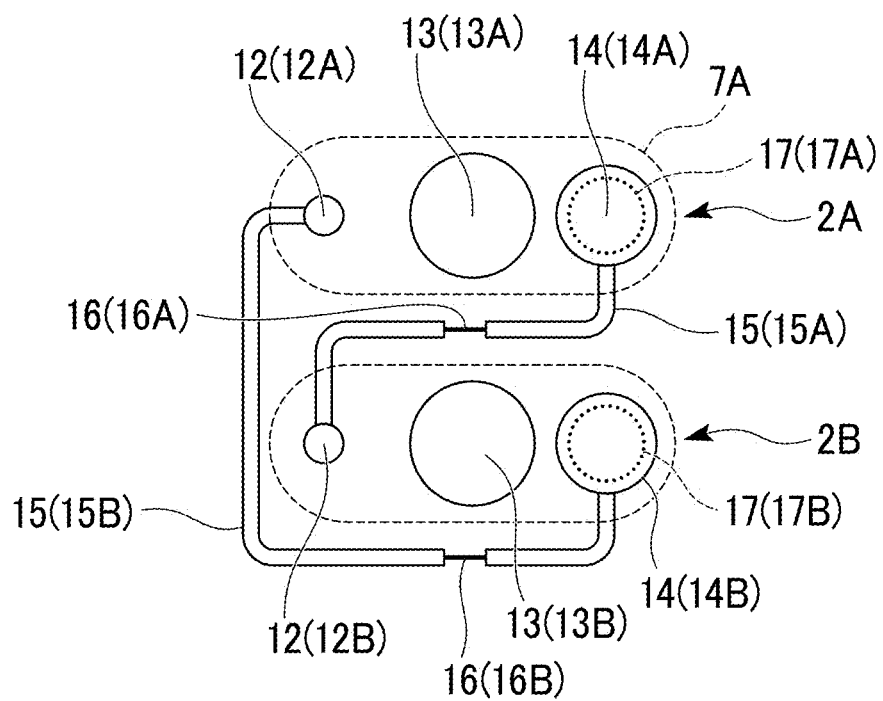
FIG. 4 is a channel constitution view of one unit in FIG. 3.

FIG. 3 is a channel constitution view (top view) of the microchannel plate (two-organ× eight-chamber connected plate) 8A in a two-connected-culture-chamber 3A-type eight-unit system, and FIG. 4 is a view describing one unit of the channel constitution (two-connected-culture-chamber) 3A in the two-organ×eight-chamber connected plate 8A in detail.

The broken lines in FIG. 4 indicate inner walls 7A of the respective culture chambers 2, and a first culture chamber 2A and a second culture chamber 2B each have an upper flow opening 12, a well 13, and a lower flow opening 14. A first lower flow opening 14A in the first culture chamber 2A and an upper flow opening 12B in the second culture chamber 2B are connected to each other through a first communication-channel 15A. A second lower flow opening 14B in the second culture chamber 2B and an upper flow opening 12A in the first culture chamber 2A are connected to each other through a second communication-channel 15B. Resistance channels 16 (16A and 16B) for adjusting the flow rates are provided in the middle of the respective communication-channels 15 (15A and 15B), the cross-sectional area of the resistance channel 16 is preferably ⅒ or less of the cross-sectional area of the communication-channel 15, and the cross-sectional area of the resistance channel 16 is significantly smaller than the cross-sectional area of the communication-channel 15. Therefore, the liquid amount of liquid flowing in the communication-channel 15 can be conveniently calculated from the cross-sectional area and length of the resistance channel 16 and pressure introduced through the pneumatic pipes 5. The wells 13 (13A and 13B) in the respective culture chambers 2 (2A and 2B) are cell-holding portions constituted of a recess portion, but the cell-holding portions are not limited to wells as long as the cell-holding portions are capable of holding cells and may be holding sheets, gels, or the like.

In addition, in the respective culture chambers 2 (2A and 2B), it is desirable to provide check valves 11 in the upper flow openings 12 (12A and 12B) and Laplace valves 17 (refer to the section of "description of Laplace valves" and the section of "regarding designs of Laplace valves" below) in the lower flow openings 14 (14A and 14B). In FIG. 4, the wells 13 (13A and 13B) are formed to have a diameter of 6 mm and a depth of 2 mm, the communication-channels 15 (15A and 15B) are formed to have a width of 1 mm and a depth of 0.5 mm, the resistance channels 16 (16A and 16B) are formed to have a width of 0.2 mm and a depth of 0.1 mm, and the Laplace valves 17 (17A and 17B) are constituted of 36 microchannels having a width of 0.1 mm and a depth of 0.016 mm (these numerical values are examples of the numerical values in the production example of FIGS. 1A and 1B, and the values are not limited thereto).

Figure 5:
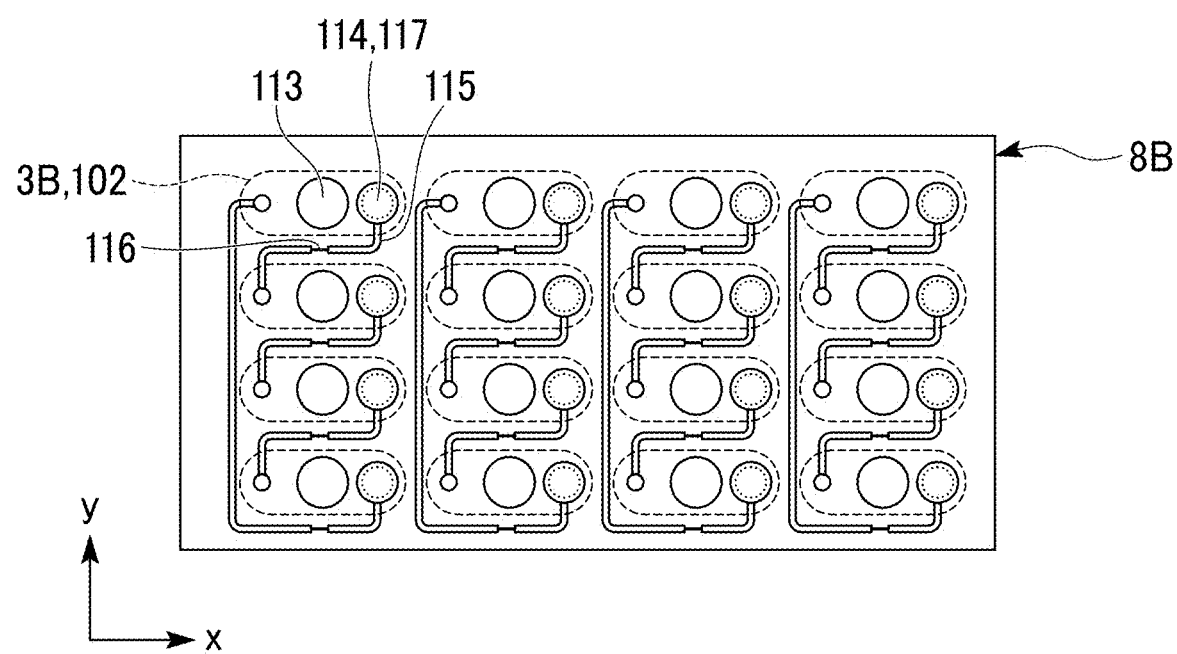
FIG. 5 is a channel constitution view of the microchannel plate in the pressure-driven cell culture apparatus shown in FIG. 2A and an example of a microchannel plate for a four-connected-culture-chamber-type four-unit system (four-organ×four-chamber connected plate).
Figure 6:
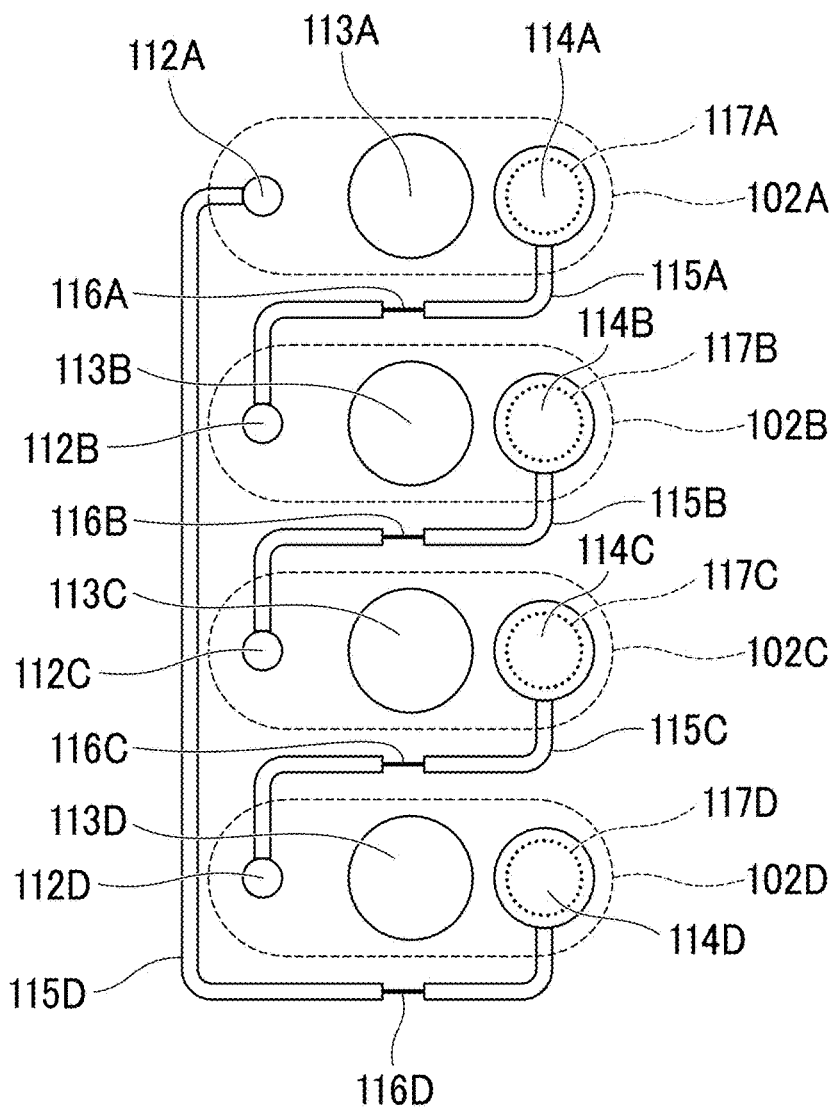
FIG. 6 is a channel constitution view of one unit in FIG. 5.

FIG. 5 is a channel constitution view of the microchannel plate 8B in a four-connected-culture-chamber-type four-unit system. FIG. 6 is a view describing in detail the channel constitution of one unit (four-connected-culture-chambers) in the microchannel plate 8B of FIG. 5. In FIG. 6, similar to in FIG. 4, wells 113 (113A, 113B, 113C, and 113D) have a diameter of 6 mm and a depth of 2 mm, communication-channels 115 (115A, 115B, 115C, and 115D) have a width of 1 mm and a depth of 0.5 mm, resistance channels 116 (116A, 116B, 116C, and 116D) have a width of 0.2 mm and a depth of 0.1 mm, and Laplace valves 117 (117A, 117B, 117C, and 117D) are constituted of 36 microchannels having a width of 0.1 mm and a depth of 0.016 mm (these numerical values are examples of the numerical values in the production example of FIGS. 1A and 1B, and the values are not limited thereto). First to fourth culture chambers 102A, 102B, 102C, and 102D respectively have first to fourth upper flow openings 112 (112A, 112B, 112C, and 112D), first to fourth wells 113 (113A, 113B, 113C, and 113D), and first to fourth lower flow openings 114 (114A, 114B, 114C, and 114D). The lower flow opening (first lower flow opening) 114A in the upstream-side culture chamber (first culture chamber) 102A and the upper flow opening (second upper flow opening) 112B in the downstream-side culture chamber (second culture chamber) 102B are connected to each other through the communication-channel (first communication-channel) 115A. The lower flow opening (fourth lower flow opening) 114D in the lowest stream-side culture chamber (fourth culture chamber) 102D and the upper flow opening (first upper flow opening) 112A in the uppermost stream-side first culture chamber (first culture chamber) 102A are connected to each other through the communication-channel (fourth communication-channel) 115D. Depending on organ models, it is also possible to branch the communication-channel from the lower flow opening (the second lower flow opening 114B or the third lower flow opening 114C) in the culture chamber (for example, the second culture chamber 102B or the third culture chamber 102C) in the middle and connect the communication-channel to the upper flow opening in the upstream-side culture chamber.

In the wells 113 (113A, 113B, 113C, and 113D) in the respective culture chambers 102A, 102B, 102C, and 102D, it is possible to mount a variety of cultured cells as organic models.

Figure 7:
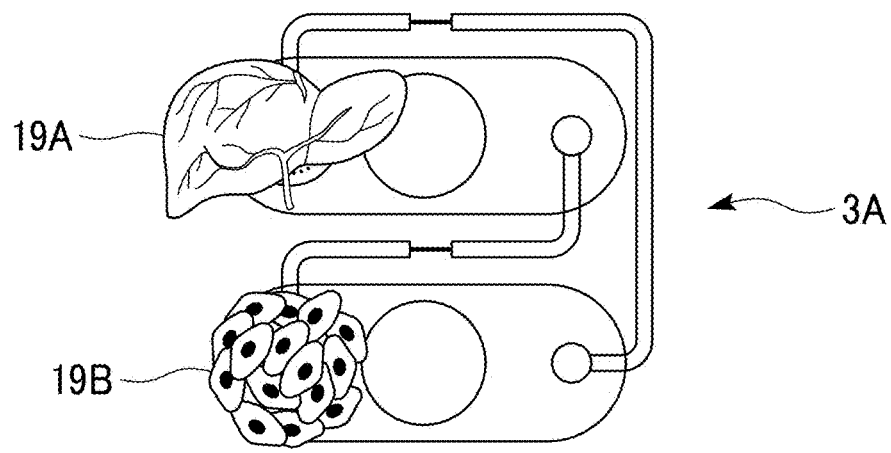
FIG. 7 shows an example in which a two-connected-culture-chamber-type multiunit system is used as a two-organ connecting model using a liver cell and a cancer cell as an organ model.

FIG. 7 shows an example in which the two-connected-culture-chamber-type eight-unit system 8A is used as the two-organ connecting model 3A using a liver cell 19A and a cancer cell 19B as an organ model.

Figure 8:
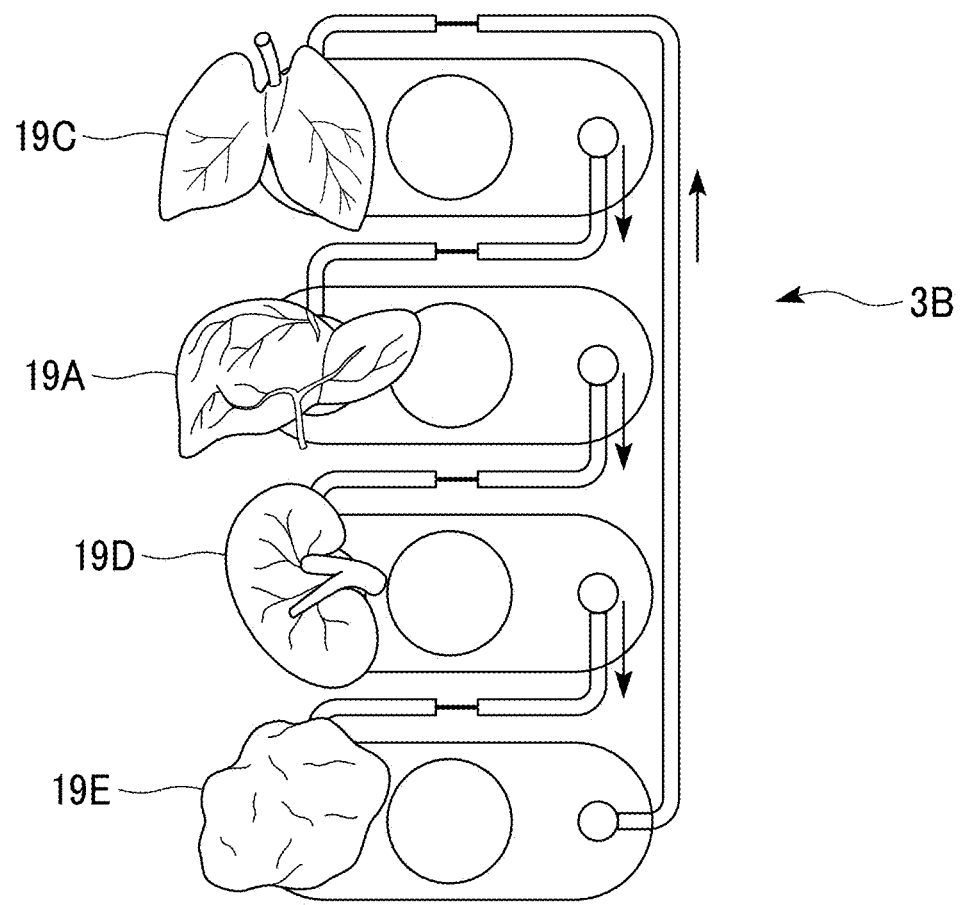
FIG. 8 shows an example in which a four-connected-culture-chamber-type multiunit system is used as a four-organ connecting model by introducing a lung cell, a liver cell, a kidney cell, and a fat cell.

FIG. 8 shows an example in which the four-connected-culture-chamber-type four-unit system 8B is used as the four-organ connecting model 3B by introducing the cells of a lung 19C, a liver 19A, a kidney 19D, and a fat 19E.

(Operating Principle of Two-Connected-Culture-Chamber 3A-Type Multiunit System)

FIGS. 9A to 9E are views describing the operating principle of a two-connected-culture-chamber 3A-based multiunit system.

As the microchannel plate, the microchannel plate 8A in the two-connected-culture-chamber 3A-type eight-unit system (two-organ×eight-chamber connected plate) shown in FIG. 3 is used.

Figure 9A:
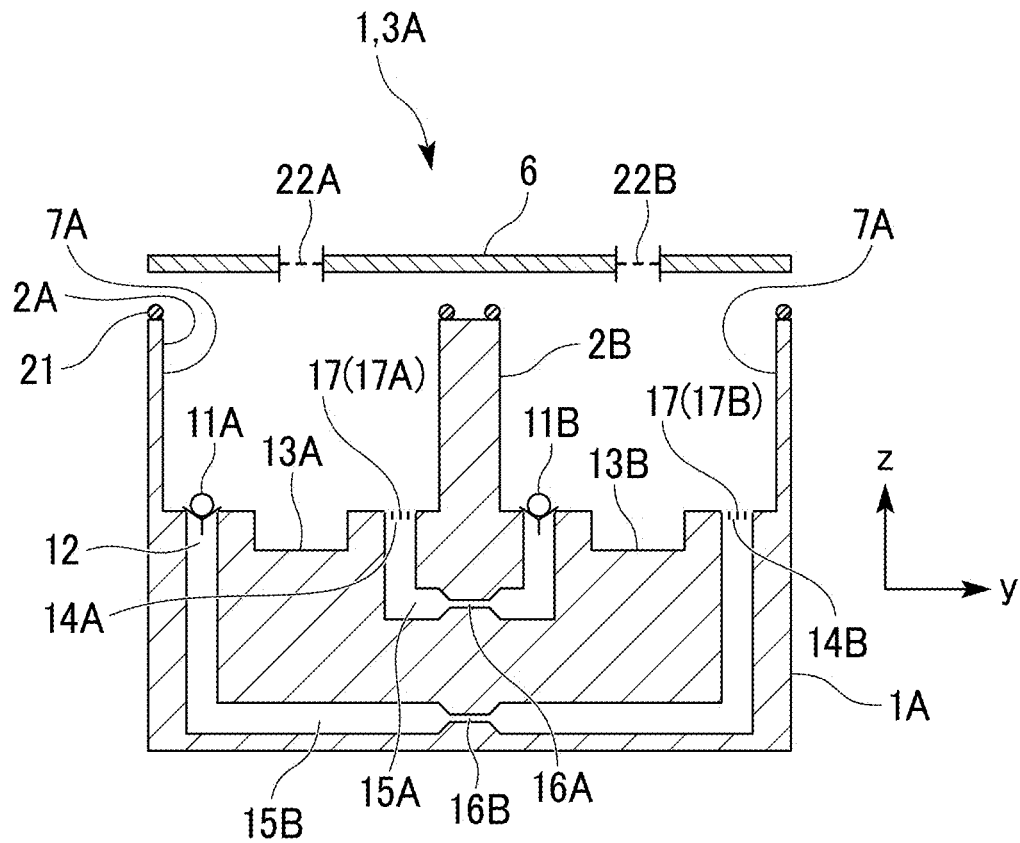
FIG. 9A is a view describing the operating principle of a two-connected-culture-chamber-based multiunit system and the operating method of the two-connected-culture-chamber-based multiunit system.

In a constitution as shown in FIG. 9A, from the bottom, the holder 9, the microchannel plate 8A, the through-hole plate 7, and the lid 6 are overlaid together and fixed using the clasps (lid portion-pressing portions or wall portion-pressing portions) 20 and 20A, thereby forming a culture container (culture apparatus) 1 for two-connected-organ culturing.

Note that, in the constitution shown in FIG. 9A, an example of a member in which the holder 9, the microchannel plate 8A, and the through-hole plate 7 are integrally formed is shown, and the member will be referred to as a main body (tank main body) 1A. In an example shown in FIG. 9A, check valves 11A and 11B are installed, and culture fluids can be circulated in the constitution.

In addition, in the integrally-formed constitution as shown in FIG. 9A, the first clasp 20 (refer to FIGS. 2A, 2B, 2C and 12A to 12C; not shown in FIGS. 9A to 9E) needs to be provided as the pressing portion (lid portion-pressing portion) of the lid 6 in the main body (tank main body) 1A. The lid 6 can be opened and closed or attached and detached by removing the first clasp 20.

Note that, in a case in which the holder 9, the microchannel plate 8A, and the through-hole plate 7 are separately provided (in the case of a non-integrally-formed constitution) as shown in FIGS. 2A, 2B, 2C, and 12A to 12C, two sets of the first clasp (lid portion-pressing portion) 20 and the second clasp (wall portion-pressing portion) 20A are installed in the holder 9, and it is also possible to open and close only the lid 6 in a state in which the microchannel plate 8A and the through-hole plate 7 are fixed using the second clasp 20A (in main body (tank main body) 1A).

When the lid 6 is closed, airtightness is secured between the lid and the main body 1A using a sealing material 21 such as an O ring. Note that, in the following steps, identical steps are carried out at the same time in all of the units.

Hereinafter, steps of culture medium circulation will be described using FIGS. 9B to 9E. Note that FIGS. 9B to 9E are views corresponding to the constitution of the two-connected-culture-chambers 3A of FIG. 9A and views describing the flow of a culture medium.

Figure 9B:
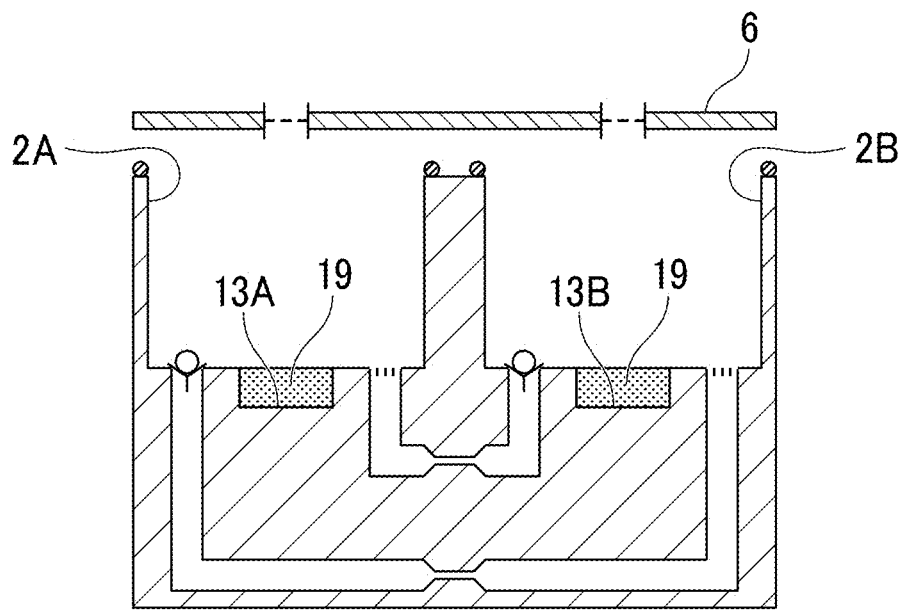
FIG. 9B is a view describing the operating principle and the operating method of the two-connected-culture-chamber-based multiunit system shown in FIG. 9A.

(1) First Step (Refer to FIG. 9B)

The lid 6 of the culture container 1 is opened, and cells 19 are seeded and adhered to the first well 13A and the second well 13B formed on the microchannel plate 8A using the through-hole plate 7.

Figure 9C:
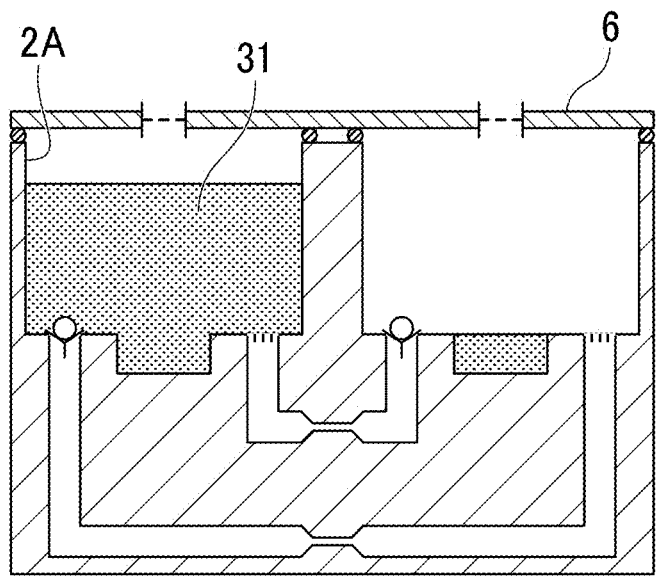
FIG. 9C is a view describing the operating principle and the operating method of the two-connected-culture-chamber-based multiunit system shown in FIG. 9A.

(2) Second Step (Refer to FIG. 9C)

The first culture chamber 2A is filled with a culture medium 31, and the lid 6 of a culture plate is closed.

Figure 9D:
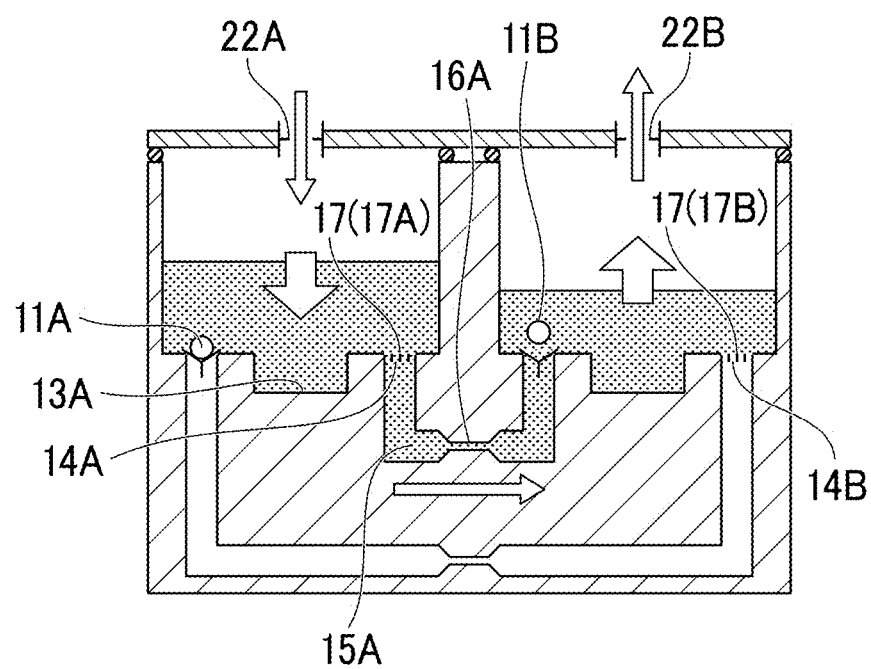
FIG. 9D is a view describing the operating principle and the operating method of the two-connected-culture-chamber-based multiunit system shown in FIG. 9A.

(3) Third Step (Refer to FIG. 9D)

The inside of the first culture chamber 2A is pressurized through a first air filter 22A, and the second culture chamber 2B is opened to atmospheric pressure through a second air filter 22B. Since the first check valve (check valve 1) 11A falls into a closed state, and the second check valve (check valve 2) 11B falls into an open state, the culture medium is sent from the first lower flow opening 14A to the second culture chamber 2B through the first communication-channel 15A. Since the first well 13A is present in a lower location than the first lower flow opening 14A, even in a case in which the inside of the first culture chamber 2A is continuously pressurized, the culture medium in the first well 13A is not depleted and remains. As described above, when a cell-holding portion including a well is provided in a culture chamber, the culture medium is not depleted, and cells are not dead.

In addition, since a Laplace valve 17 (17A) is provided at a location close to the lower flow opening 14A, due to the function of the "Laplace valve" described below, the air does not flow into the first communication-channel 15A even when the inside of the first culture chamber 2A is pressurized after the sending of the culture medium. Note that the flow rate of liquid sent is adjusted using the pressure and the resistance of the resistance channel 16A provided in the middle of the first communication-channel 15A on the microchannel plate 8A.

Figure 9E:
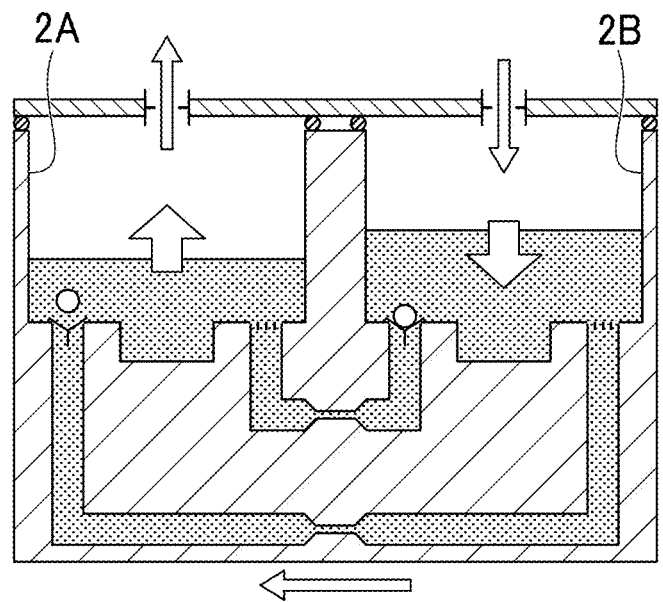
FIG. 9E is a view describing the operating principle and the operating method of the two-connected-culture-chamber-based multiunit system shown in FIG. 9A.

(4) Fourth Step (Refer to FIG. 9E)

The inside of the second culture chamber 2B is pressurized, and the inside of the first culture chamber 2A is opened to atmospheric pressure. In the same process as in the third step, the culture medium in the second culture chamber 2B is sent to the first culture chamber 2A.

(5) Culture Medium Circulation

The culture medium is circulated in the two culture chambers (between the first culture chamber and the second culture chamber) by repeating the third step and the fourth step.

(Operating Principle of Four-Connected-Culture-Chamber 3B-Type Multiunit System)

FIGS. 10A to 10G are views describing the operating principle of a four-connected-culture-chamber 3B-based multiunit system.

As the microchannel plate, the microchannel plate 8B in the four-connected-culture-chamber 3B-type four-unit system (four-organ×four-chamber connected plate) shown in FIG. 5 is used. In a constitution as shown in FIG. 10A, from the bottom, the holder 9, the microchannel plate 8, the through-hole plate 7, and the lid 6 are overlaid together and fixed using the clasps (lid portion-pressing portions or wall portion-pressing portions) 20 and 20A (refer to FIGS. 2A, 2B, 2C, and 12A to 12C), thereby forming a culture container 101 for four-connected-organ culturing.

Figure 10A:
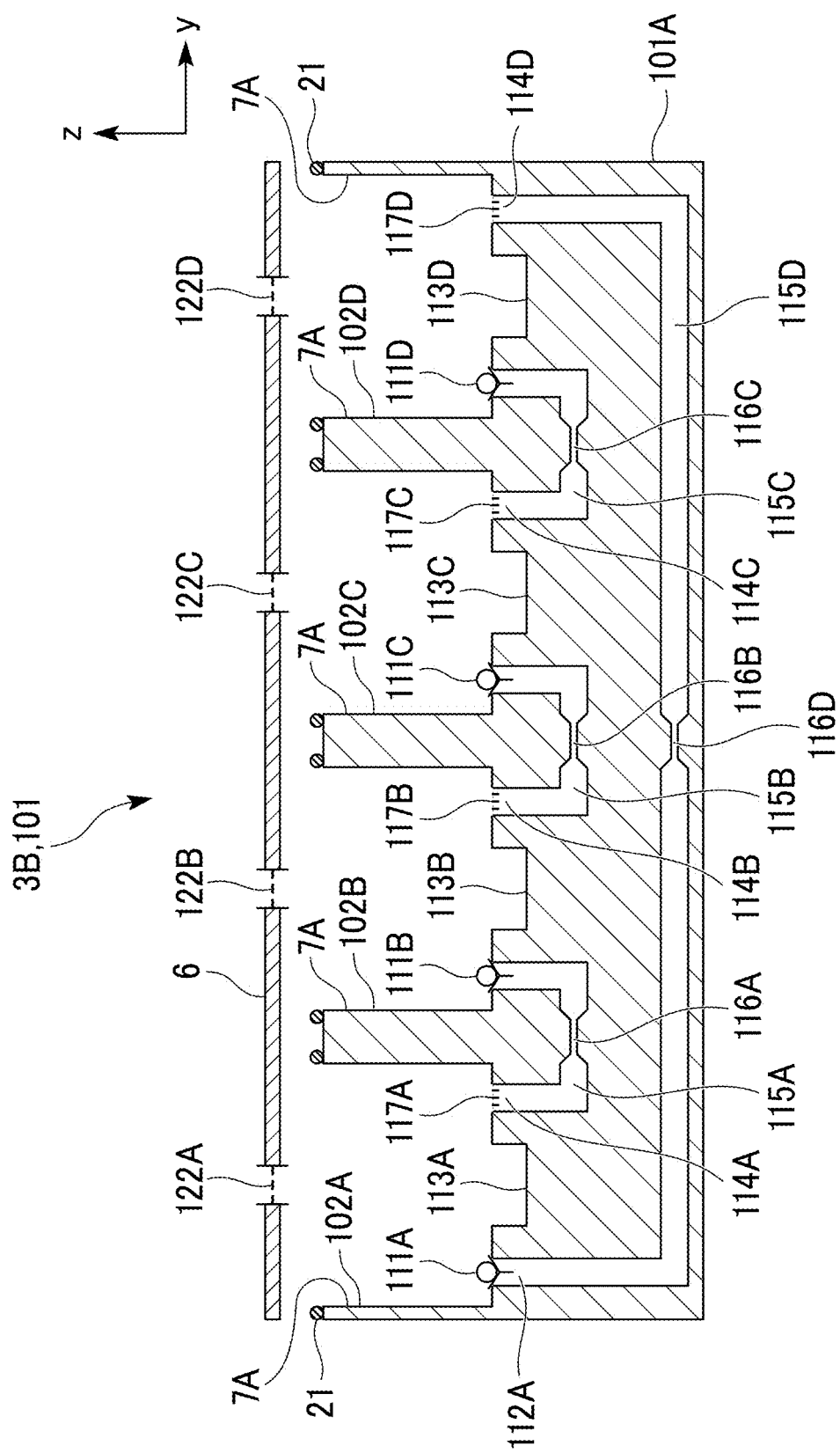
FIG. 10A is a view describing the operating principle of a four-connected-culture-chamber-based multiunit system and the operating method of the four-connected-culture-chamber-based multiunit system.

Note that, in the constitution shown in FIG. 10A, an example of a member in which the holder 9, the microchannel plate 8B, and the through-hole plate 7 are integrally formed is shown, and the member will be referred to as a main body (tank main body) 101A. In an example shown in FIG. 10A, first to four check valves 111A, 111B, 111C, and 111D are installed, and culture fluids can be circulated in the constitution.

In addition, in the integrally-formed constitution as shown in FIG. 10A, the first clasp 20 (refer to FIGS. 2A, 2B, 2C and 12A to 12C; not shown in FIGS. 10A to 10G) needs to be provided as the pressing portion (lid portion-pressing portion) of the lid 6 in the main body (tank main body) 101A. The lid 6 can be opened and closed or attached and detached by removing the first clasp 20.

Note that, in a case in which the holder 9, the microchannel plate 8A, and the through-hole plate 7 are separately provided (in the case of a non-integrally-formed constitution) as shown in FIGS. 2A, 2B, 2C, and 12A to 12C, two sets of the first clasp (lid portion-pressing portion) 20 and the second clasp (wall portion-pressing portion) 20A are installed in the holder 9, and it is also possible to open and close only the lid 6 by removing the first clasp 20 in a state in which the microchannel plate 8B and the through-hole plate 7 are fixed using the second clasp 20A (hereinafter, referred to as the main body (tank main body) 101A). When the lid 6 is closed, airtightness is secured between the lid 6 and the main body 101A using the sealing material 21 such as an O ring. In addition, in the four-connected-culture-chambers of FIGS. 12A to 12C, the first to fourth upper flow openings 112A to 112D and the first to fourth Laplace valves 117A to 117D are provided so as to correspond to FIG. 6. Note that, in the following steps, identical steps are carried out at the same time in all of the units.

Hereinafter, steps of culture medium circulation will be described using FIGS. 10B to 10G. Note that FIGS. 10B to 10E are views corresponding to the constitution of the four-connected-culture-chambers 3B of FIG. 10A and views describing the flow of a culture medium.

Figure 10B:
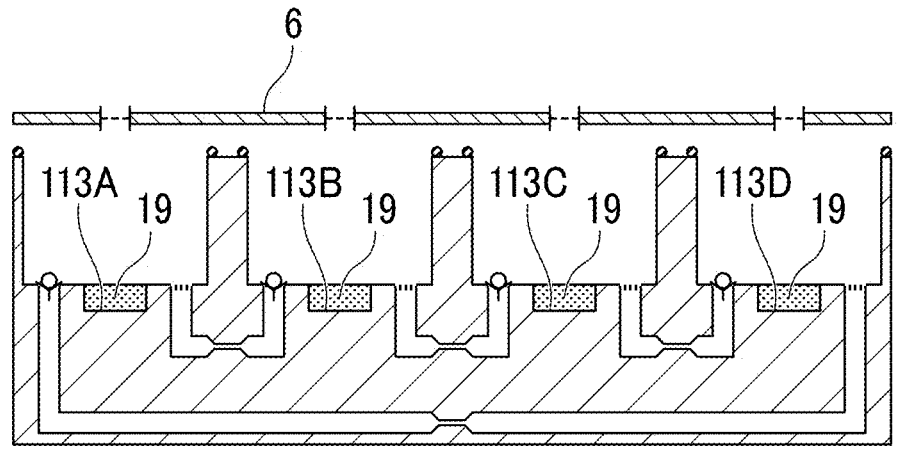
FIG. 10B is a view describing the operating principle and the operating method of the four-connected-culture-chamber-based multiunit system shown in FIG. 10A.

(1) First Step (Refer to FIG. 10B)

The lid 6 of the culture container 101 is opened, and the cells 19 are seeded and adhered to the first well 113A, the second well 113B, the third well 113C, and the fourth well 113D.

Figure 10C:
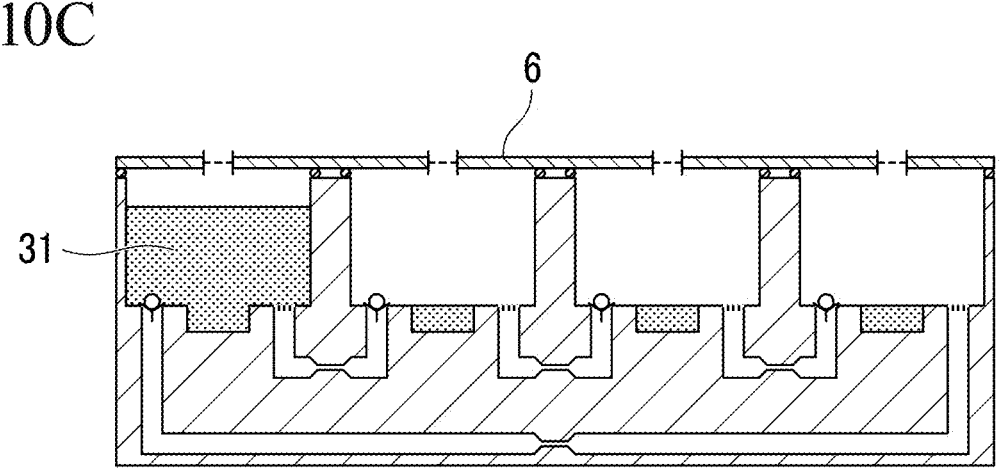
FIG. 10C is a view describing the operating principle and the operating method of the four-connected-culture-chamber-based multiunit system shown in FIG. 10A.

(2) Second Step (Refer to FIG. 10C)

The first culture chamber 102A is filled with the culture medium 31, and the lid 6 of the culture container (plate) 101 is closed.

Figure 10D:
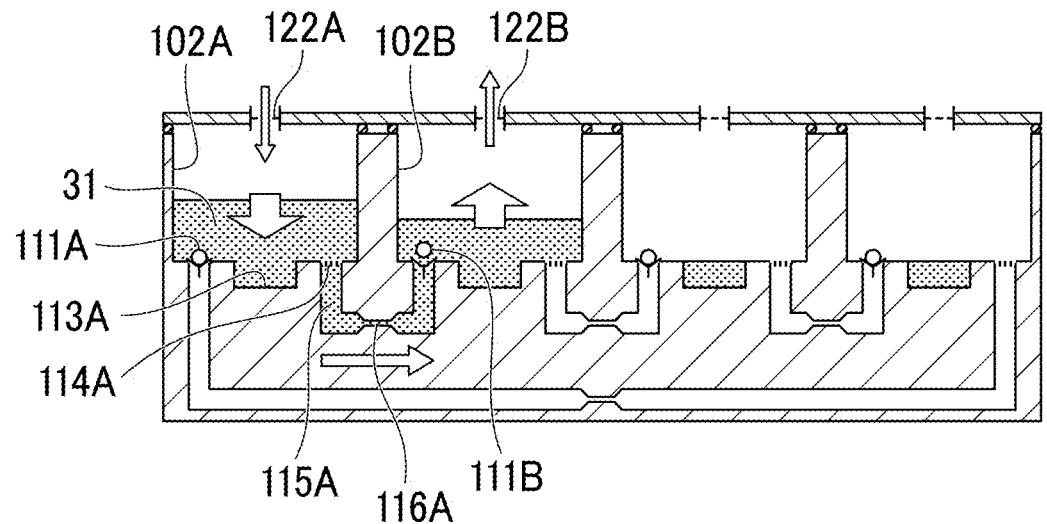
FIG. 10D is a view describing the operating principle and the operating method of the four-connected-culture-chamber-based multiunit system shown in FIG. 10A.

(3) Third Step (Refer to FIG. 10D)

The inside of the first culture chamber 102A is pressurized through a first air filter 122A, and the inside of the second culture chamber 102B is opened to atmospheric pressure through a second air filter 122B. Since the first check valve (check valve 1) 111A falls into a closed state, and the second check valve (check valve 2) 111B falls into an open state, the culture medium 31 is sent from the first lower flow opening 114A to the second culture chamber 102B through the first communication-channel 115A. Since the first well 113A is present in a lower location than the first lower flow opening 114A, even in a case in which the inside of the first culture chamber 102A is continuously pressurized, the culture medium in the first well 113A is not depleted and remains. As described above, when a cell-holding portion including a well is provided in a culture chamber, a culture medium is not depleted, and cells are not dead.

In addition, since a Laplace valve 117 (first Laplace valve 117A) is provided at a location close to the first lower flow opening 114A, due to the function of the "Laplace valve" described below, the air does not flow into the first communication-channel 115A even when the inside of the first culture chamber 102A is pressurized after the sending of the culture medium. Note that the flow rate of liquid sent is adjusted using the pressure and the resistance of the resistance channel 116A provided in the middle of the first communication-channel 115A.

Figure 10E:
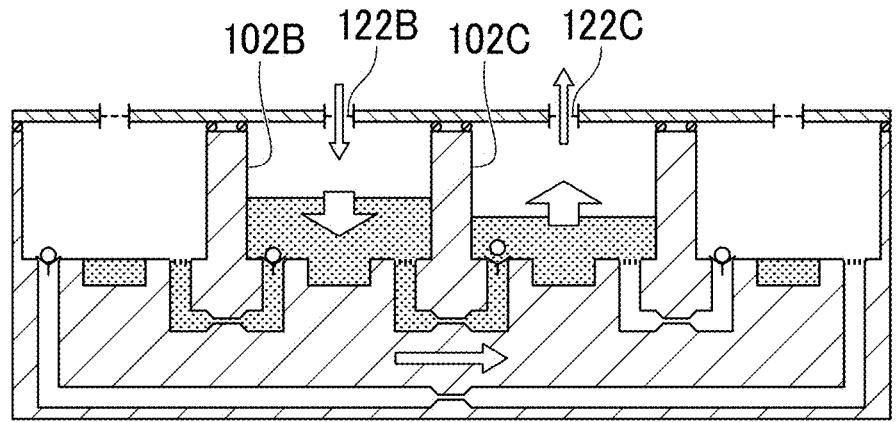
FIG. 10E is a view describing the operating principle and the operating method of the four-connected-culture-chamber-based multiunit system shown in FIG. 10A.

(4) Fourth Step (Refer to FIG. 10E)

The inside of the second culture chamber 102B is pressurized through the second air filter 122B, and the inside of the third culture chamber 102C is opened to atmospheric pressure through a third air filter 122C. In the same process as in the third step, the culture medium in the second culture chamber 102B is sent to the third culture chamber 102C.

Figure 10F:
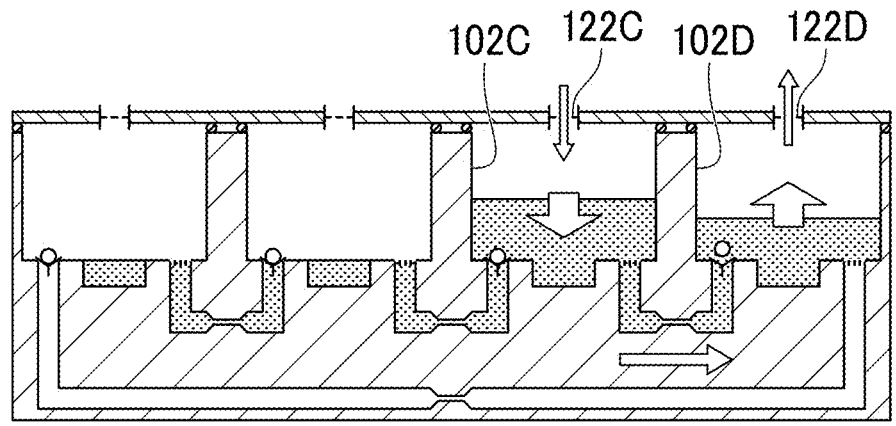
FIG. 10F is a view describing the operating principle and the operating method of the four-connected-culture-chamber-based multiunit system shown in FIG. 10A.

(5) Fifth Step (Refer to FIG. 10F)

The inside of the third culture chamber 102C is pressurized through the third air filter 122C, and the inside of the fourth culture chamber 102D is opened to atmospheric pressure through a fourth air filter 122D. In the same process as in the fourth step, the culture medium in the third culture chamber 102C is sent to the fourth culture chamber 102D.

Figure 10G:
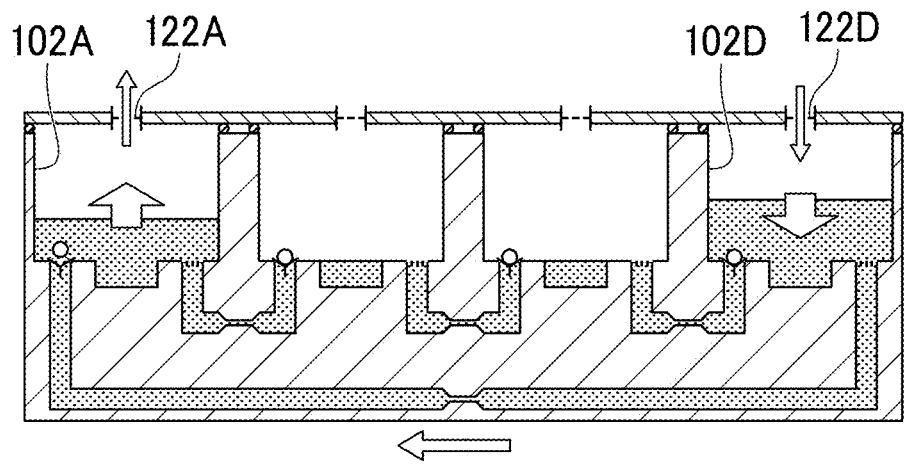
FIG. 10G is a view describing the operating principle and the operating method of the four-connected-culture-chamber-based multiunit system shown in FIG. 10A.

(6) Sixth Step (Refer to FIG. 10G)

The inside of the fourth culture chamber 102D is pressurized through the fourth air filter 122D, and the inside of the first culture chamber 102A is opened to atmospheric pressure through the first air filter 122A. In the same process as in the fifth step, the culture medium in the fourth culture chamber 102D is sent to the first culture chamber 102A.

(7) Culture Medium Circulation

The culture medium is circulated in the four culture chambers (the first to fourth chambers) by repeating the third step to the sixth step.

(Description of Laplace Valves)

Figure 11A:
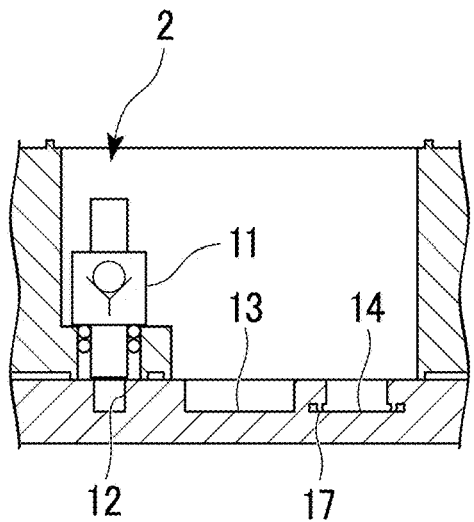
FIG. 11A is a view describing a Laplace valve.
Figure 11B:
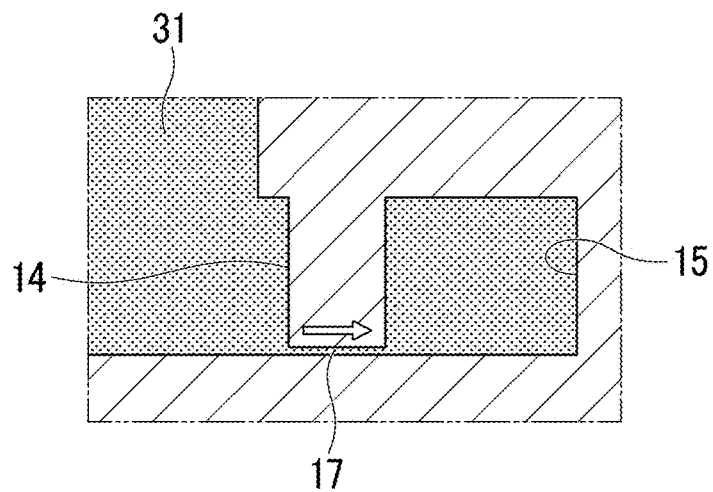
FIG. 11B is a view describing the Laplace valve.
Figure 11C:
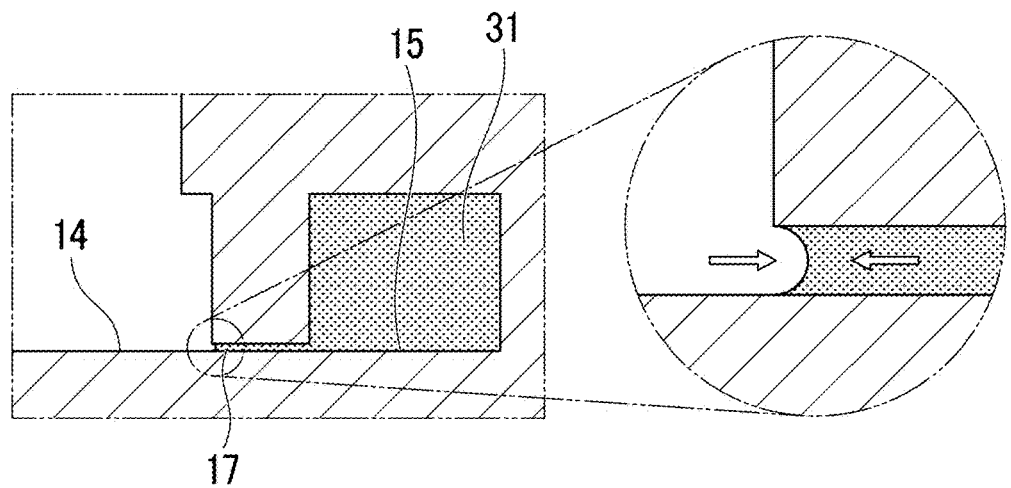
FIG. 11C is a view describing the Laplace valve.

The structure and function of the Laplace valve 17 will be described using FIGS. 11A to 11C. FIG. 11A shows a partial enlarged view of the culture chamber 2 provided with the Laplace valve 17. FIG. 11B shows a schematic view of a case in which the culture medium 31 flows into the communication-channel 15 from the lower flow opening 14 through the Laplace valve 17. FIG. 11C shows a schematic view of a case in which the Laplace valve 17 functions when the air flows into the lower flow opening 14. As shown in FIG. 11C in a fine channel, a pressure difference by interface tension, that is, Laplace pressure is generated between the culture medium and the air. In a case in which the surface of the channel gets wet by a liquid culture medium, the air is not capable of flowing into the fine channel filled with the culture medium under an air pressure condition that is lower than the Laplace pressure. Under the above-described condition, it is possible to handle the fine channel as a passive air inflow prevention mechanism. In the present specification, the air inflow prevention mechanism constituted of the fine channel will be referred to as "Laplace valve". In the microchannel plates 8A and 8B shown in FIGS. 3, 4, 5, and 6, 36 "Laplace valves" are radially provided between the lower flow openings 14 and 114 of the respective culture chambers 2A, 2B, 102A, 102B, 102C, and 102D and the communication-channels 15 and 115.

(Regarding Designs of Laplace Valves)

The designs of the above-described Laplace valve 17 will be described below.

A pressure at which the air flows into the Laplace valve (Laplace pressure or limit pressure) ($\Delta P_{Lap}$) can be calculated from Expression (1) using interface tension ($\gamma$) and the width ($w_L$) and depth ($h_L$) of the microchannel constituting the Laplace valve.

$$\Delta P_{Lap} = 2\gamma(1/w_L + 1/h_L) \quad (1)$$

A realistic pressure range for driving the culture apparatus 1 according to the present embodiment and embodiments described below is considered to be determined by pressure ranges that can be adjusted using commercially available pressure control apparatuses and the pressure resistance of cells.

When the pressure resistance of cells is approximately the upper limit of the blood pressure in living organisms (30 kPa=225 mmHg), the realistic pressure range for driving the culture apparatus 1 according to the present embodiment and embodiments described below reaches approximately 1 kPa to 30 kPa. The interface tension of a culture fluid is approximately 60 mN/m, and, in a case in which the cross-section of the microchannel constituting the Laplace valve 17 is square, that is, $w_L = h_L$, from Expression (1), the sizes of the microchannel into which the air flows at 30 kPa are estimated to be $w_L = h_L$=approximately 8 μm, and the sizes of the microchannel into which the air flows at 1 kPa are estimated to be $w_L = h_L$=approximately 240 μm.

When the sizes of the microchannel constituting the Laplace valve 17 are set to be smaller than the above-described sizes ($w_L = h_L$=8 μm at 30 kPa and $w_L = h_L$=240 μm at 1 kPa), it is possible to prevent the inflow of the air into the Laplace valve 17 when the culture apparatus is operated at a supposed pressure.

That is, when the microchannel constituting the Laplace valve 17 is formed so that the Laplace pressure $\Delta P_{Lap}$, which is a limit pressure necessary for the Laplace valve 17 to function, becomes higher than the pressure range that is used in the culture apparatus 1, it is possible to prevent the inflow of the air into the Laplace valve 17.

Note that even in a case in which the ratio between $w_L$ and $h_L$ is not 1:1, similarly, it is possible to design the sizes of the channel on the basis of Expression (1).

In examples described below, the width and depth of the microchannel are 200 μm and 25 μm, and the present apparatus is operated at a pressure that is equal to or lower than an estimated Laplace pressure of 5.4 kPa.

(Regarding Designs of Resistance Channels)

The flow rate (Q) and pressure loss ($\Delta P$) of liquid flowing through the microchannel having a rectangular cross-section have the following relationship (refer to F. M. White, Viscous Fluid Flow, McGraw-Hill Companies, Inc, Boston, 2006).

$$\Delta P = R \times Q \quad (2)$$

$$R = \frac{12\mu l}{wh^3}\left\{1 - \frac{h}{w}\left[\frac{192}{\pi^5}\sum_{i=1,3,5}^{\infty}\frac{1}{i^5}\tanh\left(\frac{i\pi w}{2h}\right)\right]\right\}^{-1} \quad (3)$$

In Expression (2) and Expression (3), $\Delta P$ represents the pressure difference between the inlet and outlet of the microchannel, R represents the channel resistance, μ represents the viscosity of fluids, l represents the length of the microchannel, w represents the width of the microchannel, and h represents the depth of the microchannel. Expression (2) and Expression (3) are satisfied under a condition of w>h.

For example, the cell culture apparatus according to the present embodiment and embodiments described below may include a resistance channel portion having a channel cross-sectional area of 1/10 or less in order to adjust flow rates in a part of the communication-channel.

At this time, a case in which a resistance channel portion in the communication-channel and portions other than the resistance channel portions in the communication-channel have the same length is considered. At this time, when the cross-sectional area of the resistance channel reaches $\frac{1}{10}$ of that of the communication-channel (portions other than the resistance channel portions in the communication-channel), the width w and the depth h reach $\frac{1}{10}^{0.5}$, and a channel resistance R in the resistance channel in Expression (3) reaches 100 times a channel resistance R in the portions other than the resistance channel in the communication-channel.

According to Expression (2), regarding the pressure loss as well, the pressure loss in the resistance channel reaches 100 times the pressure loss in the portions other than the resistance channel in the communication-channel. At this time, when the flow rate of a fluid flowing throughout the entire channel is estimated, the estimation error in a case in which the flow rate is estimated in consideration of only the resistance in the resistance channel and the pressure applied to the entire channel reaches $\frac{1}{100}$, which a permissible error.

That is, in a case in which a resistance channel portion having a channel cross-sectional area of $\frac{1}{10}$ or less is provided in order to adjust flow rates in a part of the communication-channel, there is an advantage in that it is easy to design channel networks by designing channels in consideration of only the pressure loss in the resistance channel.

Figure 12A:
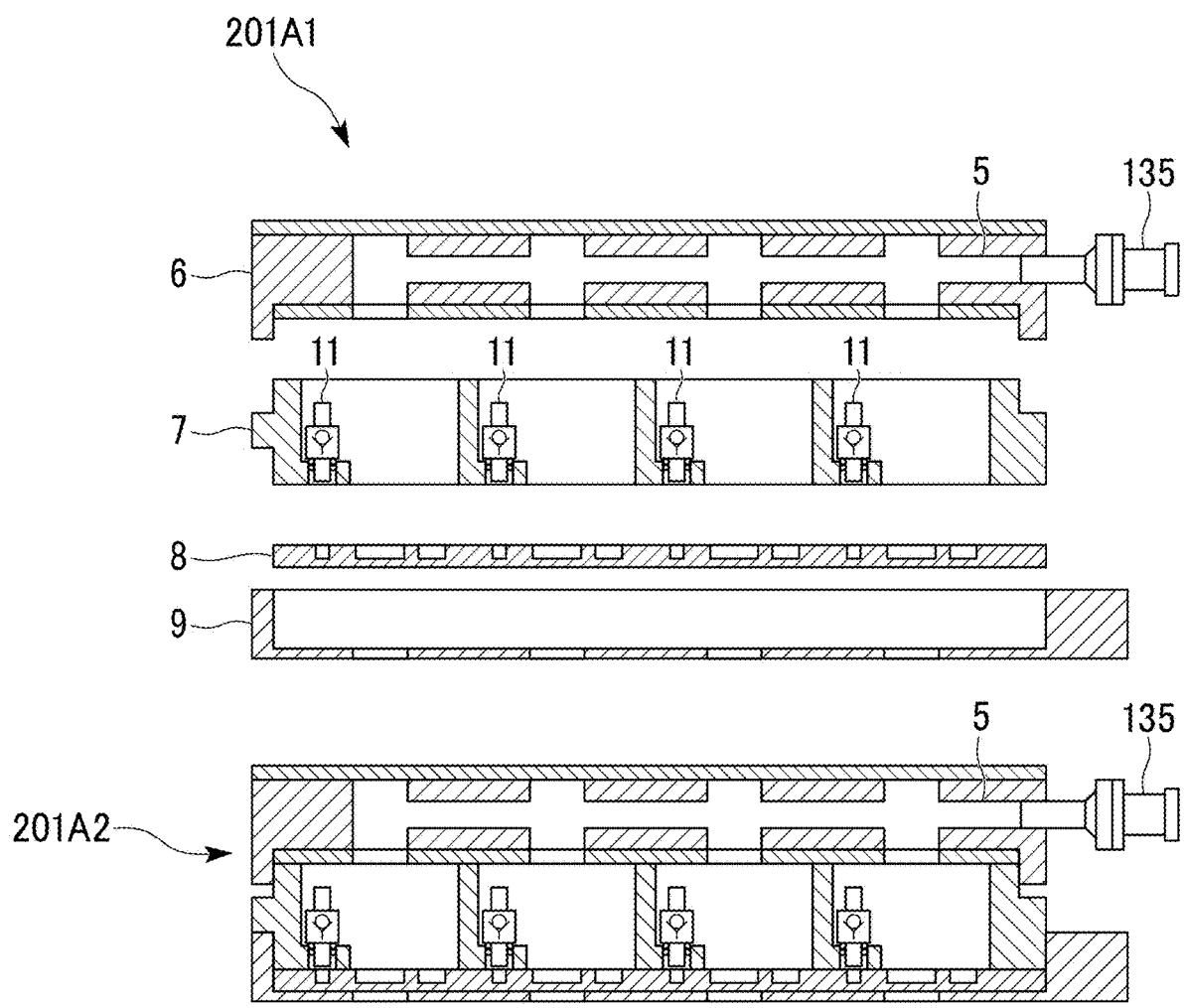
FIG. 12A shows front cross-sectional views of the example of the pressure-driven cell culture apparatus according to the first embodiment of the present invention before and after being assembled.
Figure 12B:
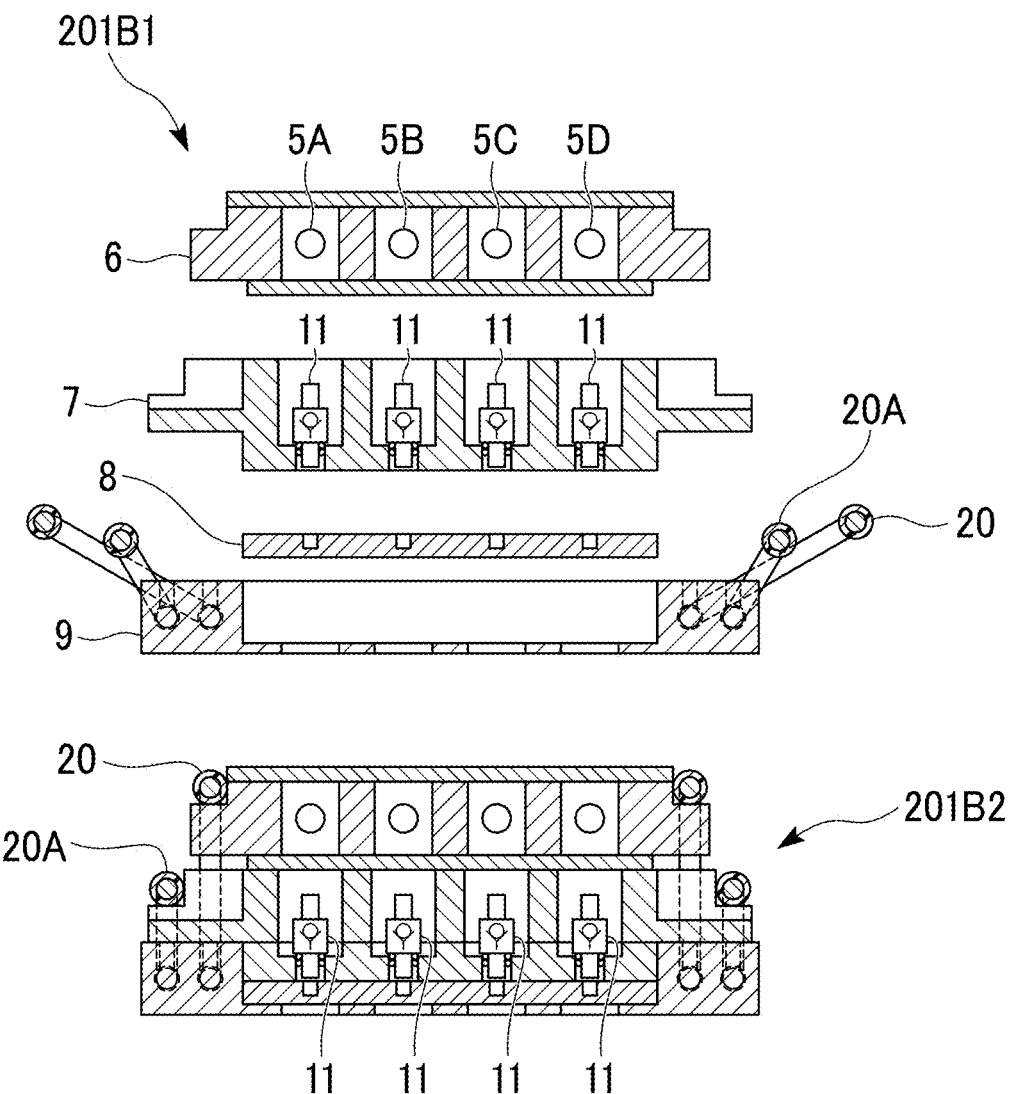
FIG. 12B shows side cross-sectional views of the example of the pressure-driven cell culture apparatus according to the first embodiment of the present invention before and after being assembled.
Figure 12C:
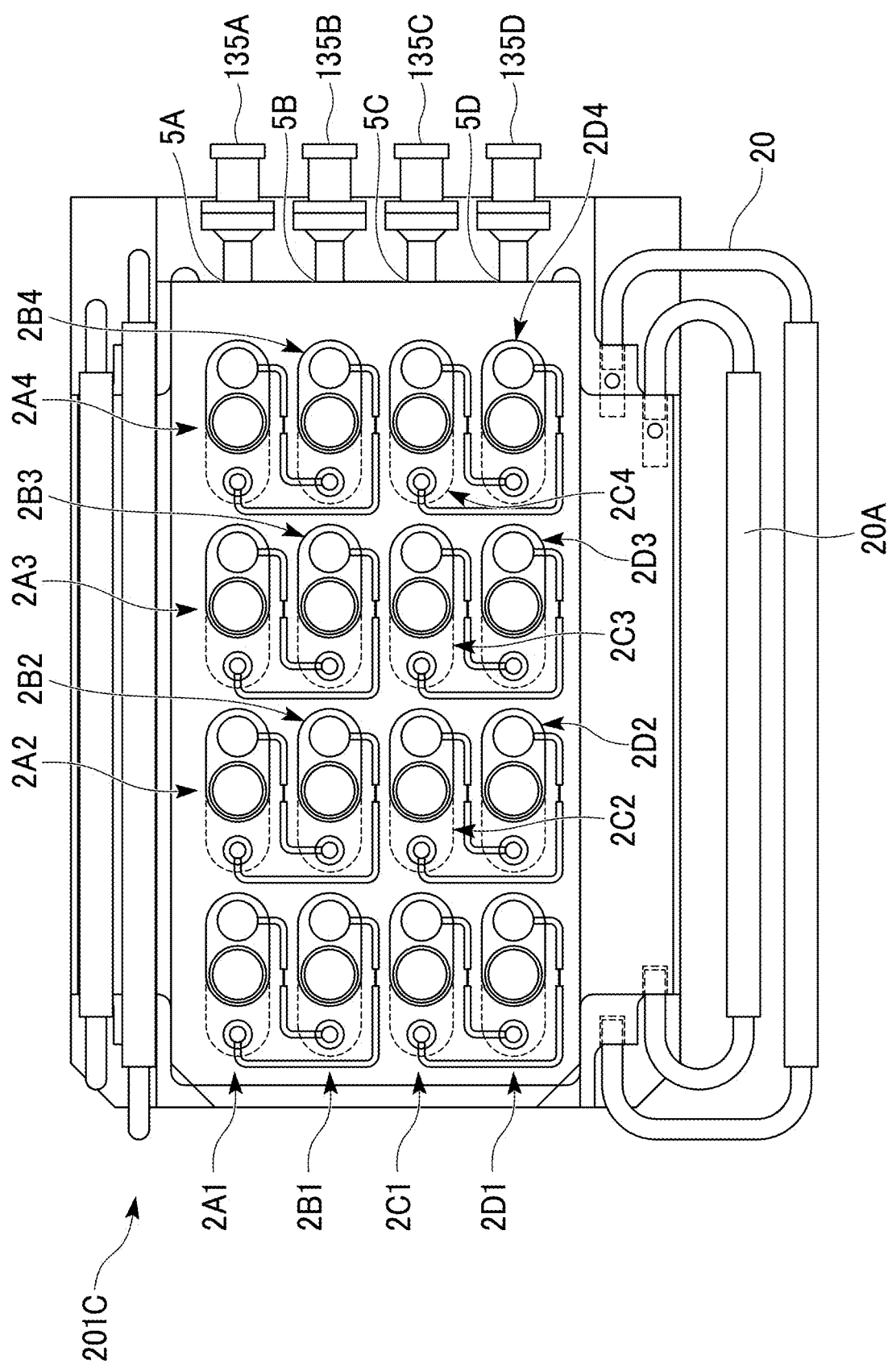
FIG. 12C is a top view of the example of the pressure-driven cell culture apparatus according to the first embodiment of the present invention.

FIGS. 12A to 12C are detailed assembly views of the cell culture apparatus 1 as the two-connected-culture-chamber 3A-type eight-unit system 8A in the cell culture apparatus 1 shown in FIGS. 2 and 3.

A front cross-sectional view (before assembly) of the cell culture apparatus 1 in FIG. 12A is represented by a reference sign 201A1, and a side cross-sectional view (before assembly) of the cell culture apparatus 1 in FIG. 12B is represented by a reference sign 201B1.

In addition, a front cross-sectional view (after assembly) of the cell culture apparatus 1 in FIG. 12A is represented by a reference sign 201A2, and a side cross-sectional view (after assembly) of the cell culture apparatus 1 in FIG. 12B is represented by a reference sign 201B2.

Furthermore, in FIG. 12C, the top view of the cell culture apparatus 1 after assembly is represented by a reference sign 201C.

Four pneumatic pipes (pressurization lines) 5A, 5B, 5C, and 5D provided in the lid 6 in FIG. 12C will be described. The uppermost pneumatic pipe (first pneumatic pipe) 5A in the top view 201C communicates with four culture chambers (a culture chamber group on a first row in the vertical direction (first direction)) 2A1, 2A2, 2A3, and 2A4 which are provided in the through-hole plate 7 and are arranged uppermost (disposed on the same row).

In the constitution, it is possible to pressurize the four culture chambers 2A1, 2A2, 2A3, and 2A4 at the same time or open the four culture chambers 2A1, 2A2, 2A3, and 2A4 to atmospheric pressure at the same time.

The other three pneumatic pipes (second to fourth pneumatic pipes) 5B, 5C, and 5D also have the same constitution as the first pneumatic pipe 5A.

Since a pair of culture chambers are connected to each other (3A type), the culture chamber 2A1 and the culture chamber 2B1 on the first row in the horizontal direction (second direction) communicate with each other.

Similarly, the culture chambers 2C1 and 2D1 on the first row in the horizontal direction communicate with each other.

As shown in the top view 201C of FIG. 12C, the other culture chambers also have the same structure.

A reference sign 135 (135A to 135D) in FIGS. 12A to 12C represents filters connected to the pneumatic pipes.

Here, the filters 135 (135A to 135D) connected to the pneumatic pipes are shown, but the filters 135 may be pressurizing apparatuses capable of sequentially pressurizing the respective culture chambers or opening the respective culture chambers to atmospheric pressure according to preset schedules.

Therefore, for example, in the third step of the two-connected-culture-chamber 3A-based multiunit system described in the section of "operating principle of two-connected-culture-chamber 3A-based multiunit system", the first pneumatic pipe (a first pneumatic pipe) 5A and the third pneumatic pipe (a third pneumatic pipe) 5C from the top in the top view 201C of FIG. 12C may be pressurized, and the second pneumatic pipe (a second pneumatic pipe) 5B and the fourth pneumatic pipe (a fourth pneumatic pipe) 5D may be opened to atmospheric pressure. In addition, in the subsequent fourth step, the first pneumatic pipe (the first pneumatic pipe) 5A and the third pneumatic pipe (the third pneumatic pipe) 5C may be opened to atmospheric pressure, and the second pneumatic pipe (the second pneumatic pipe) 5B and the fourth pneumatic pipe (the fourth pneumatic pipe) 5D may be pressurized.

In the third step described in the section of "operating principle of four-connected-culture-chamber 3B-based multiunit system" in a case in which the microchannel plate is replaced, thereby forming a four-connected-culture-chamber-type four-unit system 8B, the first pneumatic pipe from the top (the first pneumatic pipe) 5A may be pressurized, and the second pneumatic pipe (the second pneumatic pipe) 5B may be opened to atmospheric pressure.

In the subsequent fourth step, the second pneumatic pipe from the top (the second pneumatic pipe) 5B may be pressurized, and the third pneumatic pipe (the third pneumatic pipe) 5C may be opened to atmospheric pressure.

In the subsequent fifth step, the third pneumatic pipe from the top (the third pneumatic pipe) 5C may be pressurized, and the fourth pneumatic pipe from the top (the fourth pneumatic pipe) 5D may be opened to atmospheric pressure.

In the subsequent sixth step, the fourth pneumatic pipe from the top (the fourth pneumatic pipe) 5D may be pressurized, and the first pneumatic pipe (the first pneumatic pipe) 5A may be opened to atmospheric pressure.

In the above description, the cell culture apparatus 1 in which both types of the two-connected-culture-chamber 3A-type eight-unit system and the four-connected-culture-chamber 3B-type four-unit system can be used has been described, but the cell culture apparatus is not limited to the above-described example, and the cell culture apparatus can be realized as an m-connected-culture-chamber-type n-unit system (here, m and n represent integers of 2 or more).

That is, the cell culture apparatus of the present embodiment may have a constitution in which, for example, m-connected-culture-chambers in which m number of culture chambers are disposed in parallel along the vertical direction (a first direction, 2A1, 2B1, 2C1, and 2D1) in FIG. 12C are provided and n-units of the m-connected-culture-chambers are disposed in parallel along the horizontal direction (a second direction) that is disposed substantially perpendicular to the horizontal direction.

The cell culture apparatus of the present embodiment has a constitution in which the pneumatic pipe communicates with the culture chambers disposed on the same row which are constituted of n number of culture chambers disposed on the same row along the second direction (for example, the culture chambers 2A1, 2A2, 2A3, and 2A4 in FIG. 12C) and the culture chambers disposed on the same row which are constituted of n number-culture chambers can be pressured at the same time or can be opened to atmospheric pressure at the same time.

Therefore, the cell culture apparatus of the present embodiment has a constitution in which a liquid culture medium can be sent in m number of culture chambers through the communication-channel using pressure differences in the m number of the culture chambers generated using the pneumatic pipes.

When liquid culture media including different medicinal products are used in the respective units, the medicinal effects and the like of n types of medicinal products can be analyzed at once, and, when the same liquid culture medium is used, it is possible to carry out n analyses at the same time under the same condition.

In addition, in gas being used for pressure driving, it is preferable to adjust the contents of carbon dioxide and oxygen to be suitable for cell culturing.

In the above-described embodiment, an example in which the check valves 11 are used has been described, but mechanisms are not limited to check valves as long as the backward flow of liquid such as culture media can be prevented (as long as a backward flow prevention mechanism is provided).

For example, the backward flow can also be prevented by pressurizing the culture chambers on which the prevention of the backward flow is required in order to prevent the backward flow instead of using the check valves 11.

In addition, Laplace valves may also be used instead of the check valves 11.

Hereinafter, a cell culture apparatus according to a second embodiment of the present invention will be described according to the accompanying drawings.

FIGS. 13A to 13E are views describing the operating principle of a two-connected-culture-chamber-based multiunit system and the operating method of the two-connected-culture-chamber-based multiunit system in a cell culture apparatus of the present embodiment.

A difference in the present embodiment from the first embodiment is that Laplace valves (backward flow prevention Laplace valves) 317 (317A and 317B) are used as backward flow prevention mechanisms instead of the check valves 11 in the first embodiment, and the corresponding constitutions other than the backward flow prevention mechanisms are the same as those in the first embodiment and will not be described again.

Figure 13A:
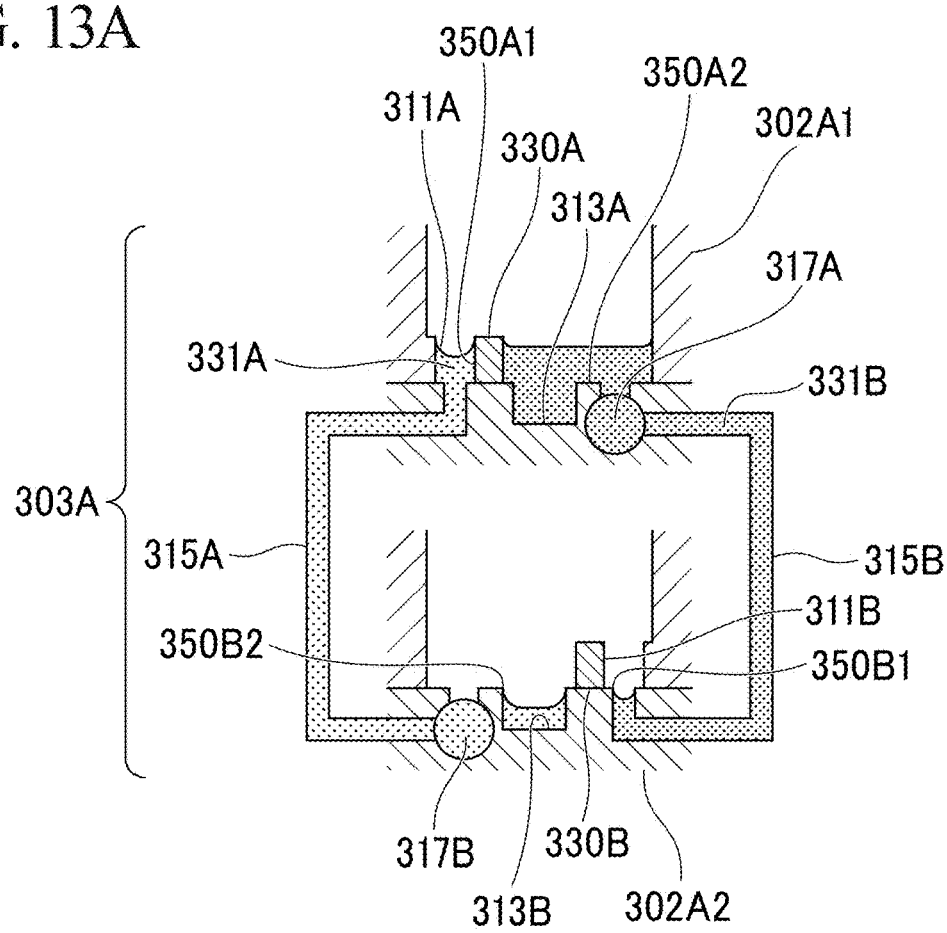
FIG. 13A is a view describing the operating principle of a two-connected-culture-chamber-based multiunit system and the operating method of the two-connected-culture-chamber-based multiunit system in a cell culture apparatus according to a second embodiment of the present invention.

FIG. 13A is a cross-sectional view of two-connected-culture-chambers 303A connected to each other.

FIGS. 13B to 13E are views corresponding the constitution of FIG. 13A and views describing the flow of a culture medium.

The two-connected-culture-chambers 303A connected to each other have a first culture chamber 302A1 and a second culture chamber 302A2.

The bottom of the first culture chamber 302A1 is divided by a first division portion 330A into a portion (a first CV portion) 350A1 provided with a first channel introduction opening 311A and a portion (a first LV portion) 350A2 provided with a first Laplace valve 317A and a first well 313A.

Similarly, the bottom of the second culture chamber 302A2 is divided by a second division portion 330B into a portion (a second CV portion) 350B1 provided with a second channel introduction opening 311B and a portion (a second LV portion) 350B2 provided with a second Laplace valve 317B and a second well 313B.

In addition, the first channel introduction opening 311A in the first culture chamber 302A1 and the second Laplace valve 317B in the second culture chamber 302A2 are connected to each other through a first channel 315A.

In addition, the first Laplace valve 317A in the first culture chamber 302A1 and the second channel introduction opening 311B in the second culture chamber 302A2 are connected to each other through a second channel 315B.

FIG. 13A shows a state in which a portion from the first channel introduction opening 311A through the first Laplace valve 317B in the first channel 315A and the second well 313B are filled with a first culture medium 331A.

In addition, FIG. 13A shows a state in which the second channel 315B and the first LV portion 350A2 provided with the first Laplace valve and the first well 313A through the second CV portion 350B1 provided with the second channel introduction opening 311B are filled with a second culture medium 331B.

In a case in which, for both the first culture medium 331A and the second culture medium 331B, the surfaces of the culture media are present in locations lower than the first division portion 330A as shown in FIG. 13A, both the first culture medium 331A and the second culture medium 331B are not capable of moving beyond the first division portion 330A. When the division portion 330A has a predetermined height as shown in FIG. 13A, the backward flow of culture media is prevented using the function of the Laplace valve 317B even without the provision of check valves.

Note that, for example, when the outlet (first channel introduction opening 311A) of the communication-channel (first channel) 315A is disposed at a higher location than the inlet (first Laplace valve 317A) of the other communication-channel (second channel) 315B, the backward flow prevention mechanisms according to the present embodiment function even without using the division portion 330A and are capable of preventing the backward flow of culture media.

Figure 13B:
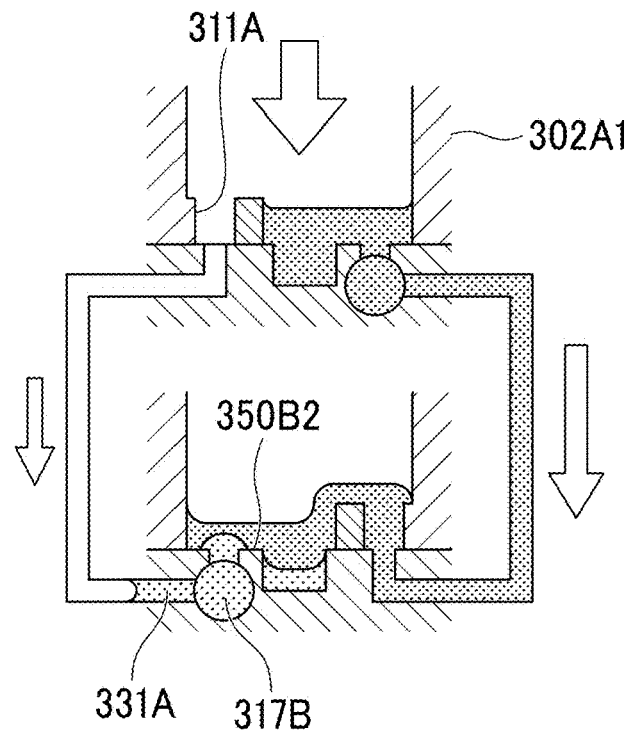
FIG. 13B is a view describing the operating principle and the operating method of the two-connected-culture-chamber-based multiunit system in the cell culture apparatus according to the second embodiment of the present invention shown in FIG. 13A.

FIG. 13B shows a view of a case in which the first culture chamber 302A1 is pressurized.

When the first culture chamber 302A1 is pressurized, the first culture medium 331A is sent from the first channel introduction opening 311A to the second Laplace valve 317B.

Similarly, when the first culture chamber 302A1 is pressurized, the second culture medium 331B is sent from the first Laplace valve 317A to the second channel introduction opening 311B.

In FIG. 13B, the first culture medium 331A present in the first channel introduction opening 311A (first CV portion 350A1) is all sent to the second Laplace valve 317B side (second LV portion 350B2).

At this time, an example of the total of the volumes of the first channel introduction opening 311A, the first channel 315A, and the second Laplace valve 317B is less than 20 μL. Compared with the volume of the first culture chamber 302A1, the total volume of the first channel introduction opening 311A, the first channel 315A, and the second Laplace valve 317B is not particularly limited. When the total volume of the first channel introduction opening 311A, the first channel 315A, and the second Laplace valve 317B is smaller than the volume of the first culture chamber 302A1, a large amount of a culture medium which has come into contact with cells present in the well (first well) 313A in the first culture chamber 302A1 flows into the second culture chamber 302A2, and thus it is possible to cause substances excreted from the cells present in the first culture chamber 302A1 to efficiently act on cells present in the second culture chamber 302A2. Therefore, the total volume of the first channel introduction opening 311A, the first channel 315A, and the second Laplace valve 317B is preferably approximately equal to or smaller than the volume of the first culture chamber, more preferably ½ or less thereof, and still more preferably 1/10 or less thereof.

Figure 13C:
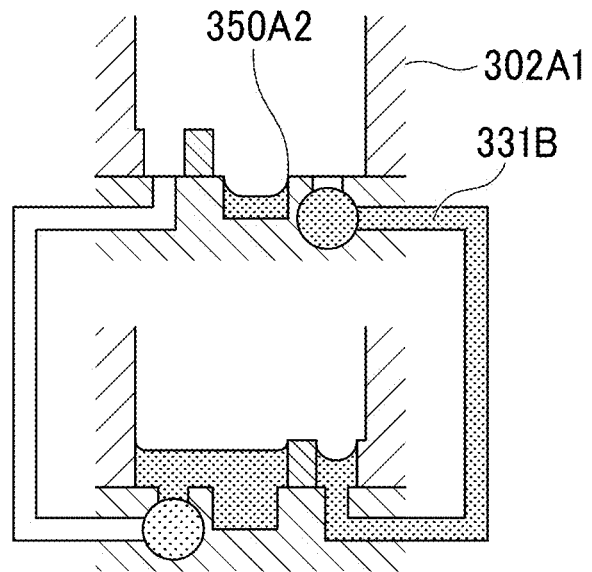
FIG. 13C is a view describing the operating principle and the operating method of the two-connected-culture-chamber-based multiunit system in the cell culture apparatus according to the second embodiment of the present invention shown in FIG. 13A.

In FIG. 13C, in the first culture chamber 302A1, the second culture medium 331B present in the first LV portion 350A2 is sent to the second culture chamber 302A2 until the air reaches the first Laplace valve 317A in the first culture chamber 302A1.

In a case in which the air reaches the Laplace valve 317A, the function of the Laplace valve works, and the sending of the second culture medium 331B is stopped.

Due to the above-described movement of the culture media, the first culture medium 331A and the second culture medium 331B are mixed together, thereby forming a mixed culture medium 331C.

Figure 13D:
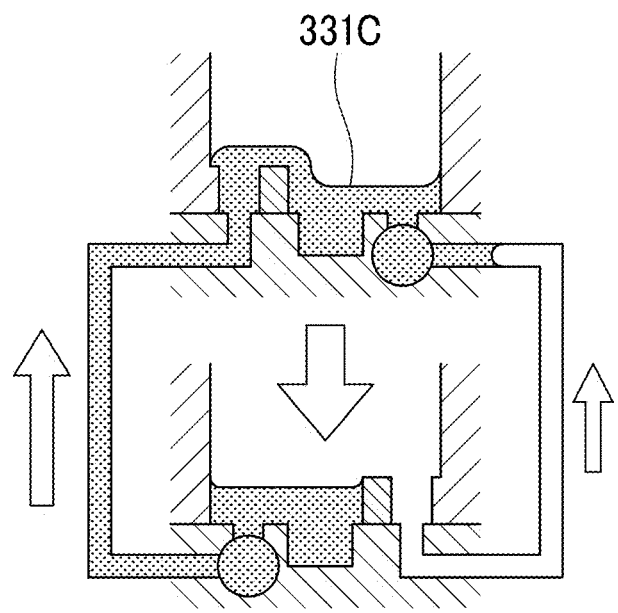
FIG. 13D is a view describing the operating principle and the operating method of the two-connected-culture-chamber-based multiunit system in the cell culture apparatus according to the second embodiment of the present invention shown in FIG. 13A.
Figure 13E:
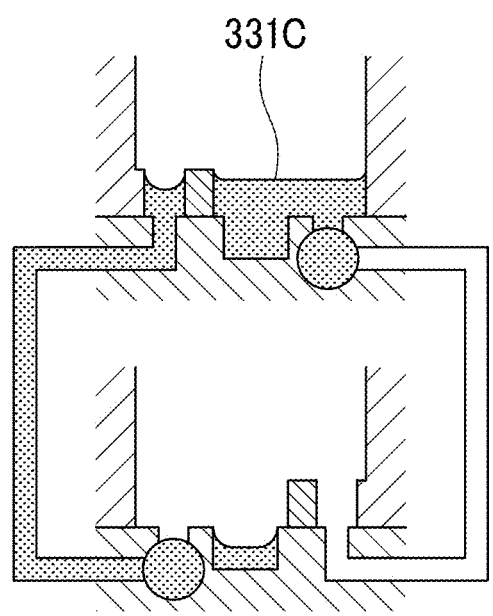
FIG. 13E is a view describing the operating principle and the operating method of the two-connected-culture-chamber-based multiunit system in the cell culture apparatus according to the second embodiment of the present invention shown in FIG. 13A.

When the second culture chamber 302A2 is pressurized as shown in FIGS. 13D and 13E, the mixed culture medium 331C is sent to the first culture chamber 302A1 from the second culture chamber 302A2 using the same mechanism as the mechanism described in the description relating to FIGS. 13B and 13C.

After that, the operation shown in FIG. 13B through the operation shown in FIG. 13D are repeated, whereby it is possible to circulate the mixed culture medium 331C and more uniformly mix the mixed culture medium 331C (a uniform mixed culture medium 331C can be formed).

Note that FIGS. 13A to 13E show an example in which the two-connected-culture-chambers 303A are used; however, in the second embodiment as well, it is also possible to use four-connected-culture-chambers as described in the first embodiment.

Even in a case in which four-connected-culture-chambers are used, similar to the example of the two-connected culture chambers 303A, it is possible to move culture media between the respective culture chambers while preventing the backward flow of the culture media, even without the provision of check valves as described in the first embodiment, by using Laplace valves (backward flow prevention Laplace valves) as the backward flow prevention mechanisms, and the mixing of the respective culture media is possible.

That is, even in four-connected-culture-chambers, culture medium circulation becomes possible by sequentially pressurizing the respective culture chambers.

Figure 13F:
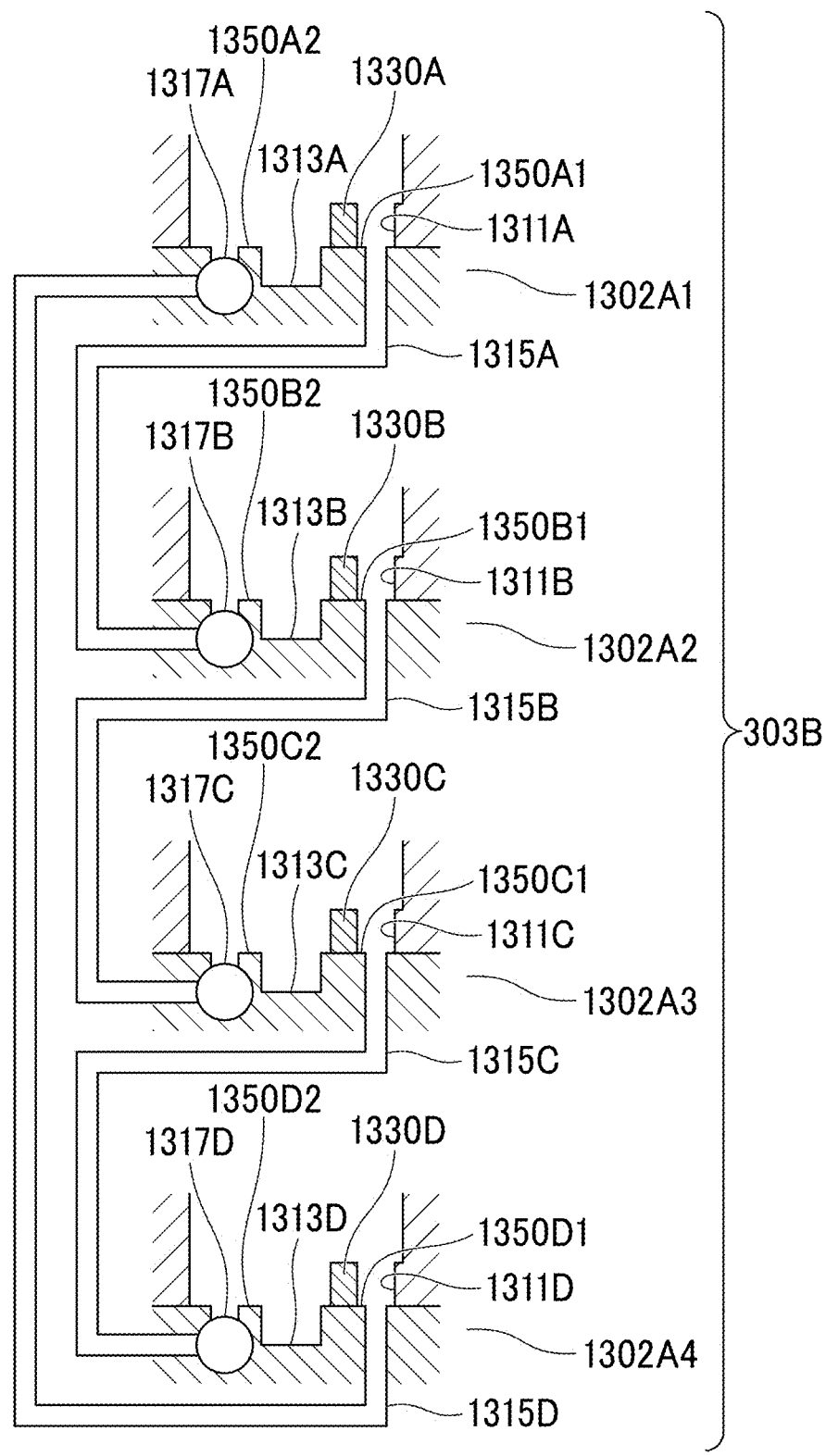
FIG. 13F is a view describing the operating principle and the operating method of the four-connected-culture-chamber-based multiunit system in the cell culture apparatus according to the second embodiment of the present invention shown in FIG. 13A.

FIG. 13F is a cross-sectional view showing an example of four-connected-culture-chambers 303B in the present embodiment.

The four-connected-culture-chambers 303B connected to each other have a first culture chamber 1302A1, a second culture chamber 1302A2, a third culture chamber 1302A3, and a fourth culture chamber 1302A4.

The bottom of the first culture chamber 1302A1 is divided by a first division portion 1330A into a portion (a first CV portion) 1350A1 provided with a first channel introduction opening 1311A and a portion (a first LV portion) 1350A2 provided with a first Laplace valve 1317A and a first well 1313A.

Similarly, the bottom of the second culture chamber 1302A2 is divided by a second division portion 1330B into a portion (a second CV portion) 1350B1 provided with a second channel introduction opening 1311B and a portion (a second LV portion) 1350B2 provided with a second Laplace valve 1317B and a second well 1313B.

Similarly, the bottom of the third culture chamber 1302A3 is divided by a third division portion 1330C into a portion (a third CV portion) 1350C1 provided with a third channel introduction opening 1311C and a portion (a third LV portion) 1350C2 provided with a third Laplace valve 1317C and a third well 1313C.

Furthermore, the bottom of the fourth culture chamber 1302A4 is divided by a fourth division portion 1330D into a portion (a fourth CV portion) 1350D1 provided with a fourth channel introduction opening 1311D and a portion (a fourth LV portion) 1350D2 provided with a fourth Laplace valve 1317D and a fourth well 1313D.

In addition, the first channel introduction opening 1311A in the first culture chamber 1302A1 and the second Laplace valve 1317B in the second culture chamber 1302A2 are connected to each other through a first channel 1315A.

In addition, the second channel introduction opening 1311B in the second culture chamber 1302A2 and the third Laplace valve 1317C in the third culture chamber 1302A3 are connected to each other through a second channel 1315B.

In addition, the third channel introduction opening 1311C in the third culture chamber 1302A3 and the fourth Laplace valve 1317D in the fourth culture chamber 1302A4 are connected to each other through a third channel 1315C.

Furthermore, the fourth channel introduction opening 1311D in the fourth culture chamber 1302A4 and the first Laplace valve 1317A in the first culture chamber 1302A1 are connected to each other through a fourth channel 1315D.

In the four connected culture chambers 303B in the present embodiment constituted as described above, cells are seeded in the first to fourth wells 1313A to 1313D, and culture media are added to the first to fourth culture chambers 1302A1 to 1302A4. In addition, similar to the example of the two-connected-culture-chambers 303A, when the first to fourth culture chambers 1302A1 to 1302A4 are sequentially pressurized, it is possible to move the culture media in the first to fourth culture chambers 1302A1 to 1302A4 while preventing the backward flow of the culture media, and the mixing of the respective culture media is possible.

When the four-connected-culture-chambers 303B according to the present embodiment are used, it is possible to cause substances excreted from cells present in the first culture chamber 1302A1 to efficiently act on cells present in the second culture chamber 1302A2. Furthermore, it is possible to cause substances excreted from the cells present in the second culture chamber 1302A2 to efficiently act on cells present in the third culture chamber 1302A3. Additionally, it is possible to cause substances excreted from the cells present in the third culture chamber 1302A3 to efficiently act on cells present in the fourth culture chamber 1302A4. In addition, it is possible to cause substances excreted from the cells present in the fourth culture chamber 1302A4 to efficiently act on the cells present in the first culture chamber 1302A1.

As described above, when the four-connected-culture-chambers 303B according to the present embodiment are used, it is possible to sequentially cycle the substances excreted from the cells disposed in the first to fourth culture chambers 1302A1 to 1302A4 among these culture chambers.

According to the four-connected-culture-chambers 303B of the present embodiment, it is possible to evaluate influences among cells in the same manner as in the four-organ connecting model 3B by, for example, introducing cells which serve as models of the lung 19C, the liver 19A, the kidney 19D, and the fat 19E as in the four-connected-culture-chamber-type four-unit system 8B shown in FIG. 8 relating to the first embodiment.

The volumes, sizes, and the like of the respective constituent elements such as the first to fourth culture chambers 1302A1 to 1302A4, the first to fourth Laplace valves 1317A to 1317D, the first to fourth channel introduction openings 1311A to 1311D, and the first to fourth channels 1315A to 1315D in the four-connected-culture-chambers 303B of the present embodiment may be the same as those in the example described in the section of the two-connected-culture-chambers 303A of the present embodiment.

In the present embodiment, examples of the two-connected-culture-chambers and the four-connected-culture-chambers have been described, but the number of culture chambers is not limited thereto as long as the number of the culture chambers is two or more.

Hereinafter, a cell culture apparatus according to a third embodiment of the present invention will be described according to the accompanying drawings.

Figure 14:
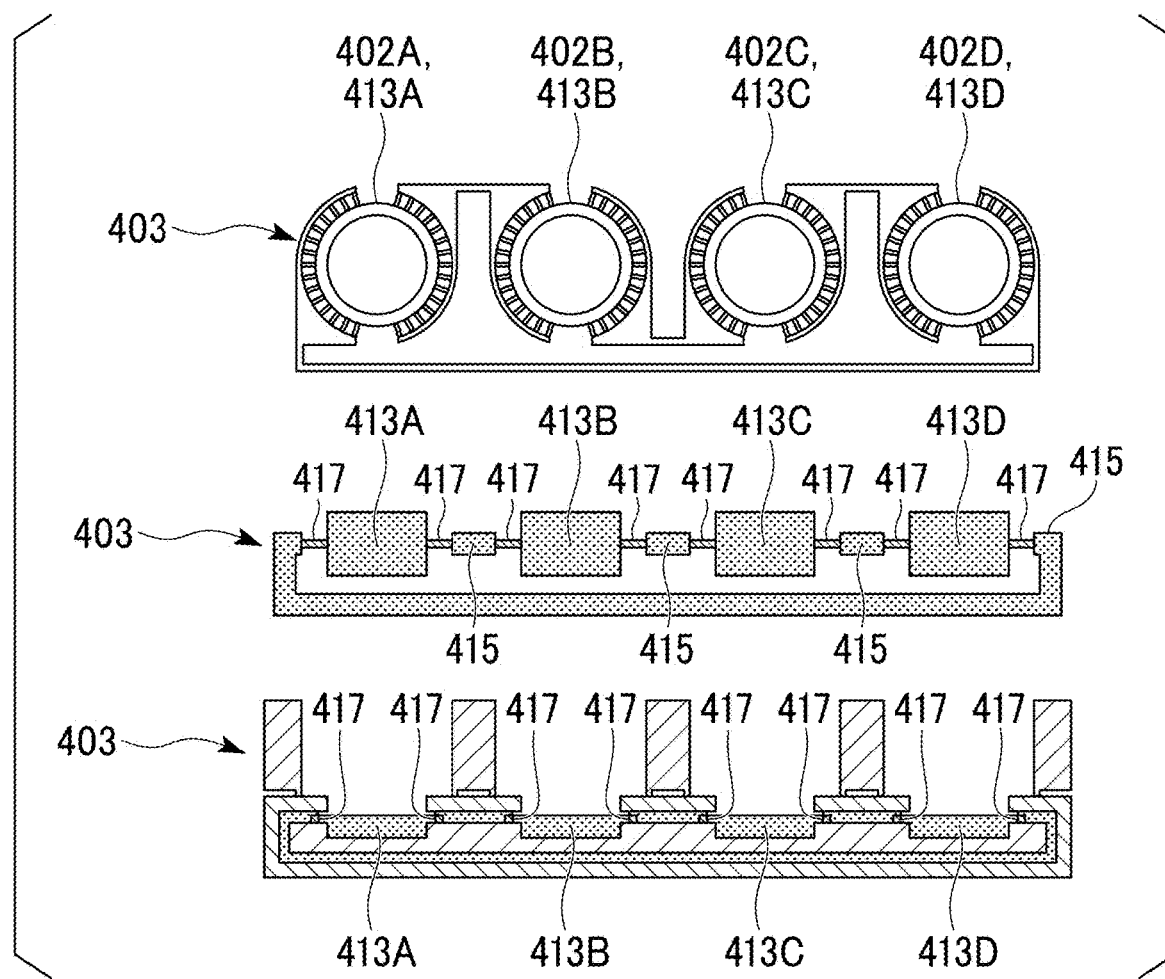
FIG. 14 is a view describing the operating principle of a four-connected-culture-chamber-based multiunit system and the operating method of the four-connected-culture-chamber-based multiunit system in a cell culture apparatus according to a third embodiment of the present invention.
Figure 15:
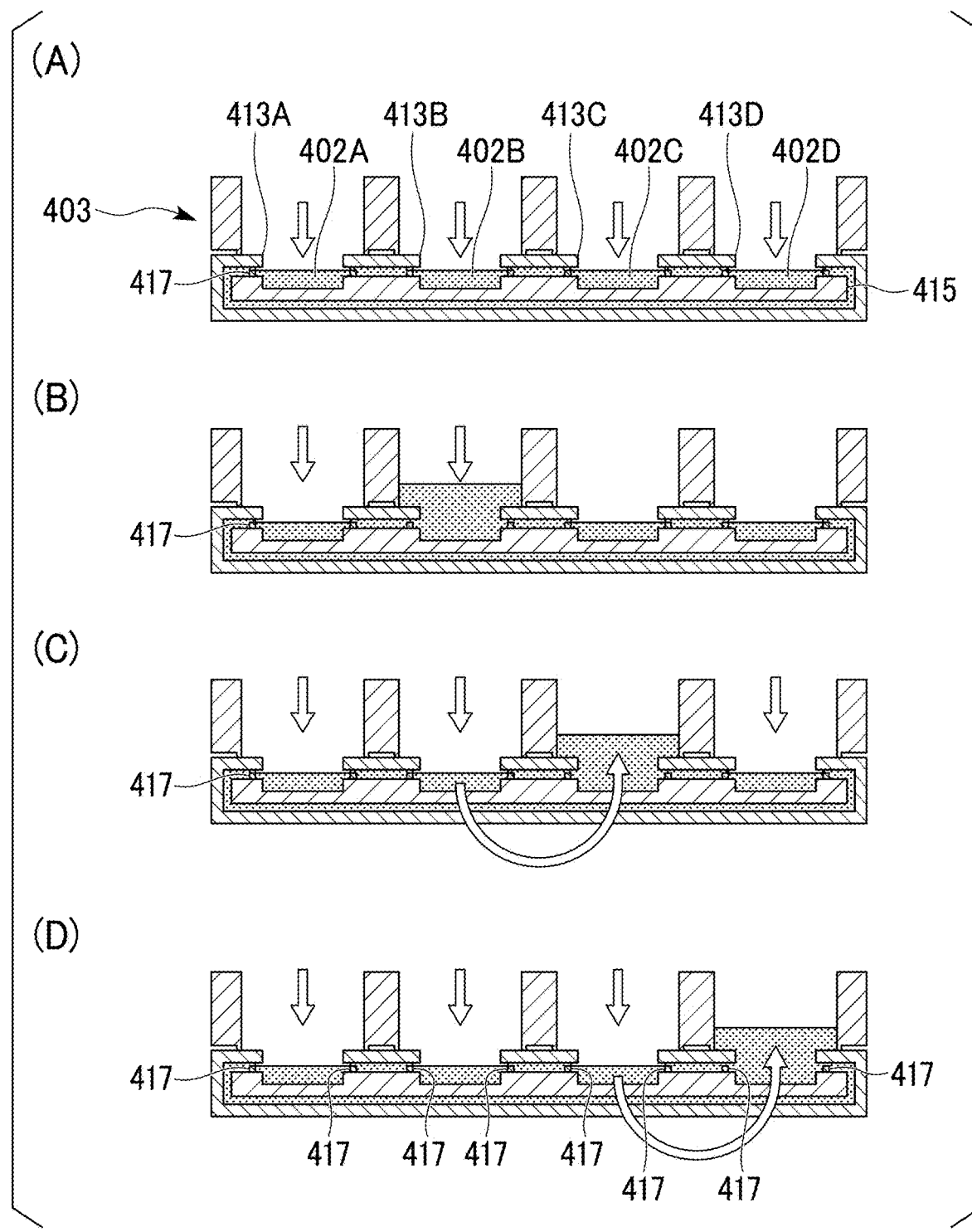
FIG. 15 is a view describing the operating principle of the four-connected-culture-chamber-based multiunit system and the operating method of the four-connected-culture-chamber-based multiunit system in a cell culture apparatus according to the third embodiment of the present invention.

FIGS. 14 and 15 are views describing the operating principle of a four-connected-culture-chamber-based multiunit system and the operating method of the four-connected-culture-chamber-based multiunit system in a cell culture apparatus of the present embodiment.

Differences in the present embodiment from the first embodiment are that (1) Laplace valves (backward flow prevention Laplace valves) 417 are used as the backward flow prevention mechanisms instead of the check valves 11 in the first embodiment and (2) four-connected-culture-chambers as shown in FIG. 14 are used, and the corresponding constitutions other than (1) and (2) are the same as those in the first embodiment and will not be described again.

An air pressure-driven culture medium circulation-type cell culture apparatus according to the present embodiment, which is shown in FIGS. 14 and 15, will be described below.

FIG. 14 shows, from the top, (1) a top view showing channels of four-connected-culture-chambers 403 according to the present embodiment, (2) a simplified view of the linkage between the constituent elements in the four-connected-culture-chambers 403, and (3) a schematic cross-sectional view of the four-connected-culture-chambers 403.

FIG. 15 is a schematic operation view of an air pressure-driven culture medium circulation-type cell culture apparatus in a case in which the four-connected-culture-chambers 403 according to the present embodiment are used.

As shown in part (A) of FIG. 15, in the four-connected-culture-chambers 403, first to fourth culture chambers 402A to 402D are provided.

In addition, the first to fourth culture chambers 402A to 402D are respectively provided with first to fourth wells 413A to 413D.

First, as shown in part (A) of FIG. 15, cells 419 are seeded and adhered in individual wells of the first to fourth wells 413A to 413D.

Next, as shown in part (B) of FIG. 15, a culture medium 431 is poured into the second well 413B.

Next, as shown in part (C) of FIG. 15, the first culture chamber 402A, the second culture chamber 402B, and the fourth culture chamber 402D are pressurized.

Note that the pressures applied at this time are substantially equal in the first to fourth culture chambers 402A to 402D and are lower pressures than the Laplace pressure in the Laplace valve 417 provided in the four-connected-culture-chambers 403.

At this time, as shown in part (C) of FIG. 15, the culture medium surfaces of a culture medium present in the first culture chamber 402A and the fourth culture chamber are present at a lower location than the location of the Laplace valves, and thus the culture medium does not flow out.

In addition, since the pressurization is carried out at a pressure lower than the Laplace pressure, the Laplace valve 417 functions, and the air does not flow into the channel 415.

Furthermore, since the first culture chamber 402A and the second culture chamber 402B are pressurized at the same pressure, the culture medium does not move from the second culture chamber 402B to the first culture chamber 402A.

As shown in part (C) of FIG. 15, the culture medium 431 poured into the second culture chamber 402B is sent only to the third culture chamber 402C which is opened to the atmosphere.

Next, when the pressurization operation of the culture chamber as shown in part (C) of FIG. 15 is repeated as shown in part (D) of FIG. 15, the one-way circulation of the culture medium is possible.

When the pressurization operation of the culture chamber and the one-way circulation of the culture medium are repeated, it is possible to accelerate the mixing of culture media in the respective chambers.

In the present embodiment, an example in which the first to fourth culture chambers 402A to 402D are provided has been described, but the same operation is possible as long as the number of culture chambers is three or more.

The culture chamber according to the present embodiment may have three or more culture chambers and is not limited to four-connected-culture-chambers.

EXAMPLES

Next, the cell culture apparatus 1 according to the embodiments of the present invention will be described in detail by describing examples. Note that the following examples are specific examples to which the present invention is applied and do not limit the present invention in any way.

Figure 16A:
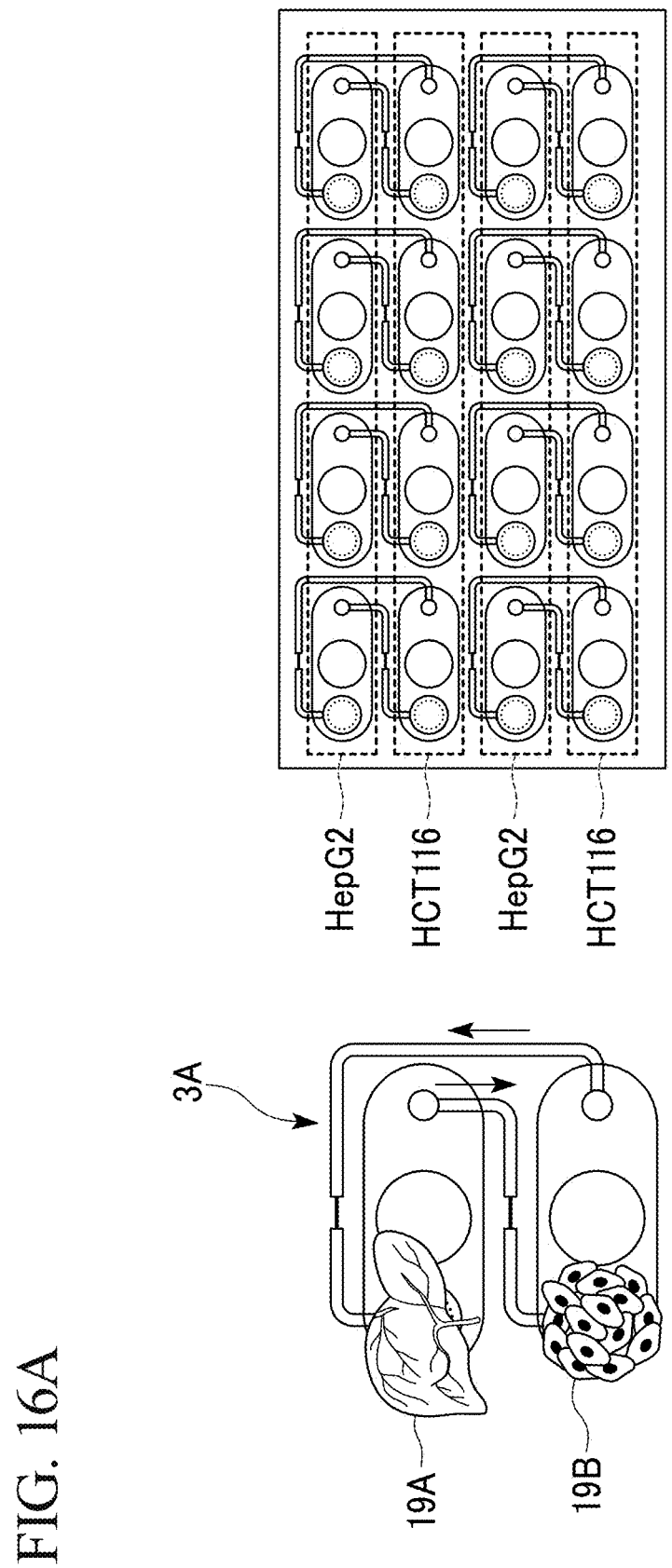
FIG. 16A is a view of liver cancer cells HepG2 (liver models) and large intestine cancer cells HCT116 (large intestine cancer cells) disposed in a culture plate in an example.

As a co-culture model of a liver and a cancer structure, the culturing of liver cancer cells HepG2 (liver models) and large intestine cancer cells HCT116 (large intestine cancer cells) was carried out using a two-organ×eight-chamber connected culturing system (cell culture apparatus). The disposition of the respective cells in a culture plate is shown in FIG. 16A. Note that the drawing shown in FIG. 16A corresponds to the two-organ connecting model 3A of FIG. 7.

As shown in FIG. 16A, the liver cancer cells HepG2 (liver models) were disposed along the horizontal direction of the cell culture apparatus and were disposed in a culture chamber group on the first row in the vertical direction.

The large intestine cancer cells HCT116 were disposed along the horizontal direction of the cell culture apparatus and were disposed in a culture chamber group on the second row in the vertical direction.

In addition, the liver cancer cells HepG2 (liver models) were disposed along the horizontal direction of the cell culture apparatus and were disposed in a culture chamber group on the third row in the vertical direction.

The large intestine cancer cells HCT116 were disposed along the horizontal direction of the cell culture apparatus and were disposed in a culture chamber group on the fourth row in the vertical direction.

Figure 16B:
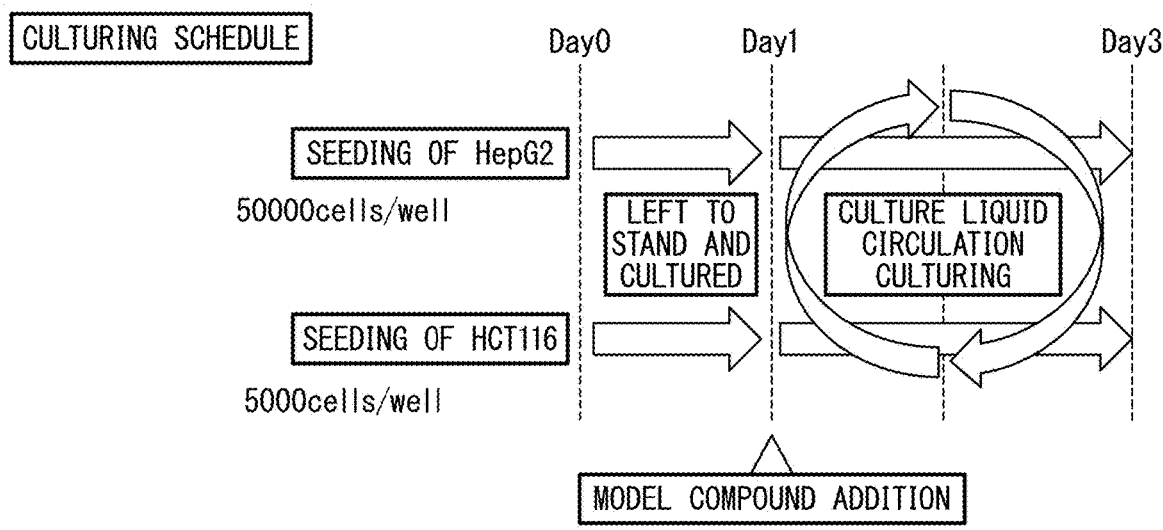
FIG. 16B is a view showing a culturing schedule of the liver cancer cells HepG2 (liver models) and the large intestine cancer cells HCT116 (large intestine cancer cells) in the example.

In addition, a culturing schedule of the liver cancer cells HepG2 (liver models) and the large intestine cancer cells HCT116 (large intestine cancer cells) is shown in FIG. 16B.

Wells used to culture HepG2 were coated with Collagen Type I (Cell Matrix, manufactured by Nitta Gelatin Inc.) according to a protocol provided by the manufacturer.

Wells used to culture the large intestine cancer cells HCT116 were coated with 50 µl of a Fibronectin solution (28.3 µg/mg).

After the coating with the Fibronectin solution, the respective wells were washed with a culture medium, and the cells were seeded. At this time, the HepG2 cells were suspended in a William's E culture medium at a concentration of one million cells/ml, the HCT116 was suspended in a MEM culture medium at a concentration of 100,000 cells/ml, and the respective solutions were added to the wells in a liquid amount of 50 ml.

After three hours from the seeding of the cells, 300 ml of the culture medium was added to each of the culture chambers in which the respective wells were present. At this time, the William's E culture medium was added to the chambers including HepG2, and the MEM culture medium was added to the chambers including HCT116.

After the cells were left to stand and cultured overnight, the culture media in the respective chambers were replaced with 300 ml of the William's E culture medium, and circulation culturing was carried out.

The circulation culturing was carried out by repeating the pressurization of the chambers to which HepG2 was added and the chambers to which HCT116 was added at 4 kPa every ten minutes.

Figure 17A:
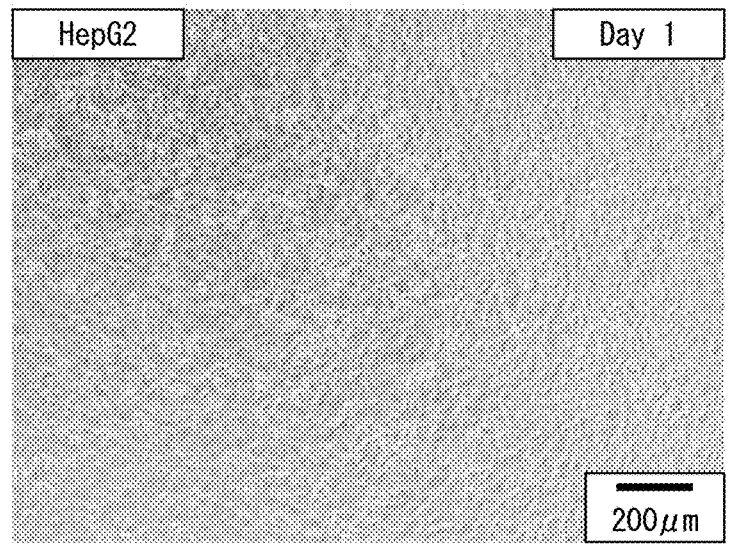
FIG. 17A is a photograph of HepG2 cells immediately before the initiation of circulation culturing in an example (Day 1).

A photograph of the HepG2 cells immediately before the initiation of the circulation culturing (Day 1) is shown in FIG. 17A.

Figure 17B:
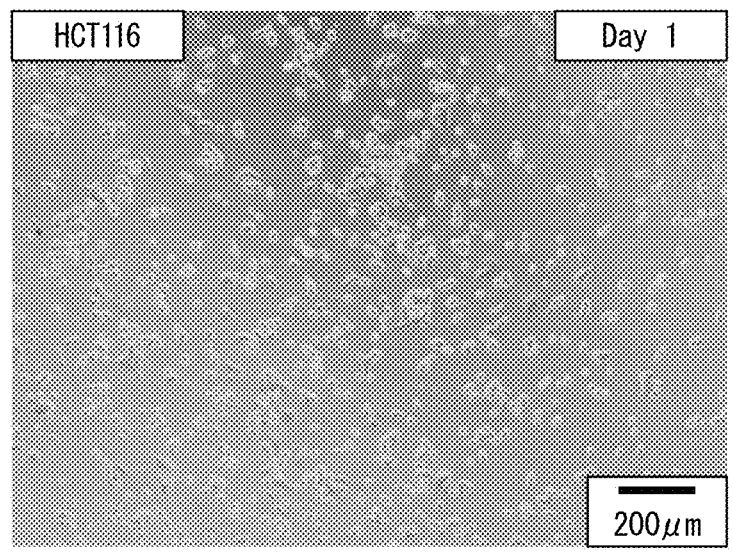
FIG. 17B is a photograph of HCT116 cells immediately before the initiation of the circulation culturing in an example (Day 1).

A photograph of the HCT116 cells immediately before the initiation of the circulation culturing (Day 1) is shown in FIG. 17B.

Figure 17C:
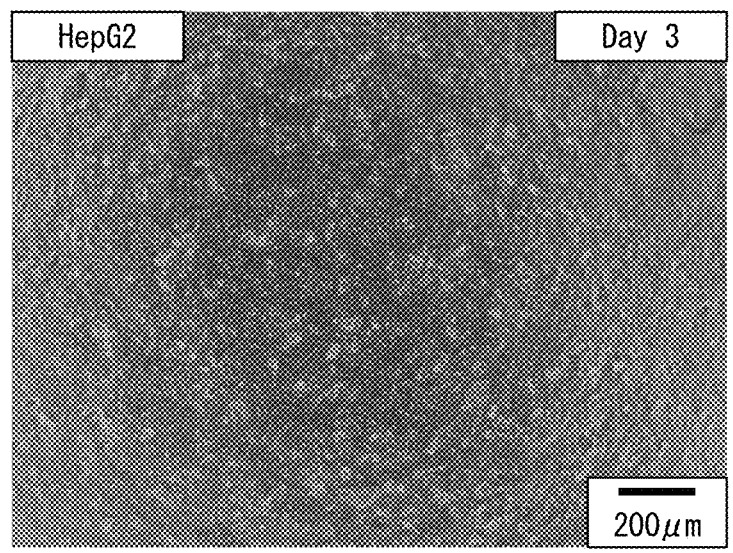
FIG. 17C is a photograph of the HepG2 cells after carrying out the circulation culturing for 48 hours in the example.

A photograph of the HepG2 cells after carrying out the circulation culturing for 48 hours is shown in FIG. 17C.

Figure 17D:
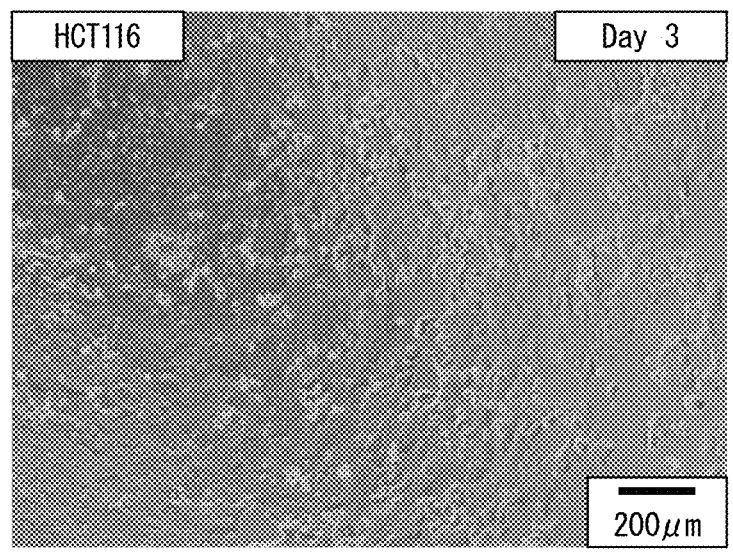
FIG. 17D is a photograph of the HCT116 cells after carrying out the circulation culturing for 48 hours in the example.

A photograph of the HCT116 cells after carrying out the circulation culturing for 48 hours is shown in FIG. 17D.

An appearance in which both the HepG2 cells and the HCT116 cells were adhered to the bottom surfaces of the wells during the circulation culturing was observed, and an appearance in which the number of the HCT116 cells increased was observed.

When model compounds are added to the culture medium (300 ml of the William's E culture medium) that is used during the circulation culturing, it is possible to evaluate the influence of the model compounds on liver and cancer cells at the same time and to evaluate the influences in a state in which the interactions between organs are reflected on a real-time basis.

INDUSTRIAL APPLICABILITY

According to the cell culture apparatus and the cell culture method of the present invention, it is possible to analyze the medicinal effects or toxicity of medicinal products or chemical products and pharmacokinetics such as absorption, distribution, metabolism, and excretion using cultured cells. In addition, the present invention can be used for the analyses of medicinal products or chemical products as an alternative animal biomass.

DESCRIPTION OF REFERENCE NUMERAL 1, 101 Cell culture apparatus (Body-on-a-Chip unit)
1A, 101A Main body (tank main body)
2, 2A, 2A1 to 2A4, 2B, 2B1 to 2B4, 2C1 to 2C4, 2D1 to 2D4, 102A to 102D, 302A1, 302A2, 402A to 402D, 1302A1 to 1302A4 Culture chamber (organ model culture chamber)
3A, 303A Two-connected-culture-chambers (two-organ connecting model, two-connected-culture-chamber-type PDMS plate)
3B, 303B, 403 Four-connected-culture-chambers (four-organ connecting model, four-connected-culture-chamber-type PDMS plate)
4, 15, 15A, 15B, 115, 115A to 115D, 315A, 315B, 415 Communication-channel (microchannel, organ-connecting microchannel)
5, 5A to 5D Pneumatic pipe (pressurization line, pressure pipe line)
6 Lid (pressurizing lid)
7 Through-hole plate
7A Wall surface (wall portion, wall surface of culture chamber, inner walls of through-hole plate and chamber)
8 Microchannel plate
8A Two-organ×eight-chamber connected plate (two-connected-culture-chamber-type eight-unit system, bottom plate)
8B Four-organ×four-chamber connected plate (four-connected-culture-chamber-type four-unit system, bottom plate)
9 Holder (base body portion)
11, 11A, 11B, 111A to 111D Check valve
12, 12A, 12B, 112 Upper flow opening
13, 13A, 13B, 113, 113A to 113D, 313A, 313B, 413A to 413D, 1313A to 1313D Well
14, 14A, 14B, 114, 114A to 114D Lower flow opening
16, 16A, 16B, 116 Resistance channel
17, 17A, 17B, 317, 317A, 317B, 417, 417A to 417D, 1317A to 1317D Laplace valve
19A Liver
19B Cancer
19C Lung
19D Kidney
19E Fat
20 First clasp (lid portion-pressing portion, pressing member)
20A Second clasp (wall portion-pressing portion, pressing member)
21 Sealing material
22A, 22B, 122A to 122D Air filter
135, 135A to 135D Filter (pressurizing apparatus)
201A1 Front cross-sectional view of cell culture apparatus (before assembly)
201B1 Side cross-sectional view of cell culture apparatus (before assembly)
201A2 Front cross-sectional view of cell culture apparatus (after assembly)
201B2 Side cross-sectional view of cell culture apparatus (after assembly)
201C Top view of cell culture apparatus
311A, 311B, 1311A to 1311D Channel introduction opening
330A, 330B, 1330A to 1330D Division portion
331A, 331B, 431 Culture medium
331C Mixed culture medium
350A1, 350B1, 1350A1 to 1350D1 CV portion (portion provided with channel introduction opening)
350A2, 350B2, 1350A2 TO 1350D2 LV portion (portion provided with Laplace valve and well)
419 CELL

The invention claimed is:
1. A cell culture apparatus, comprising:
a connected culture container comprising n number of units, where each of the n number of the units consists of m number of culture chambers and one or more communication-channels, wherein each of the culture chambers comprises a cell-holding portion that holds seeded cells, wherein the m number of the culture chambers are disposed in parallel along a first direction and communicating with each other by the one or more communicating-channels, wherein each of the culture chambers is configured to store liquid culture media, wherein the n number of units are disposed in parallel along a second direction that is different from the first direction, wherein m is an integer of two or more, and n is an integer of two or more, a plurality of pneumatic pipes communicating same-row-disposed culture chambers that are disposed on a same row along the second direction with each other in the connected culture container, the pneumatic pipes being configured to pressurize the same-row-disposed culture chambers at the same time or open the same-row-disposed culture chambers to atmospheric pressure at the same time, the pneumatic pipes being configured to send the liquid culture media to each of the culture chambers through the communication-channels using pressure differences in each of the culture chambers, and further comprising a Laplace valve configured at portions connected to the one or more communication-channels and the culture chambers, to prevent flows of air using interface tension to the communication-channels from the culture chambers.

2. The cell culture apparatus according to claim 1, further comprising:

a backward flow prevention mechanism configured to control flow directions from the communication-channels toward the m number of the culture chambers, the backward flow prevention mechanism being provided at an end of the communication-channels or in the communication-channels, wherein the backward flow prevention mechanism is a check valve, a backward flow prevention Laplace valve, a division portion dividing the culture chamber with a portion provided with a channel introduction opening of a communication-channel of the one or more communication-channels and a portion provided with the LaPlace valve, or a first channel introduction opening of a communication-channel of the one or more communication-channels disposed at a higher location than an inlet of the other communication-channels.

3. The cell culture apparatus according to claim 1, wherein each of the m number of the culture chamber comprises a chamber structure formed in a container-shaped tank main body storing liquid culture media and a lid portion configured to open an opening-portion of the tank main body, or to close air-tightly the opening-portion of the tank main body.

4. The cell culture apparatus according to claim 3, further comprising:

a lid portion-pressing portion configured to hold the lid portion so as to be pressed toward the tank main body, wherein the lid portion-pressing portion comprises a base body portion that supports the tank main body and a pressing member that presses the lid portion toward the tank main body supported by the base body portion and further comprising a pressing member configured to hold the lid portion so as to be pressed toward the tank main body, wherein the pressing member is a clasp, or a base body portion that supports the tank main body and a pressing member that presses the lid portion toward the tank main body supported by the base body portion.

5. The cell culture apparatus according to claim 4, wherein the tank main body comprises a wall portion and a bottom plate including the communication-channels.

6. The cell culture apparatus according to claim 5, further comprising:

a wall portion-pressing portion that holds the wall portion so as to be pressed toward the bottom plate, wherein the wall portion-pressing portion comprises a pressing member that presses the wall portion toward the base body portion and the bottom plate supported by the base body portion.

7. The cell culture apparatus according to claim 1, wherein, when a width of a microchannel constituting the Laplace valve is represented by $w_L$, a depth of the microchannel is represented by $h_L$, the interface tension is represented by $\gamma$, and a Laplace pressure of the Laplace valve is represented by $\Delta P_{Lap}$, the Laplace pressure is expressed by an expression of $\Delta P_{Lap}=2\gamma(1/w_L+1/h_L)$, and the microchannel is constituted so that the Laplace pressure $\Delta P_{Lap}$ becomes larger than a pressure applied to the connected culture container.

8. The cell culture apparatus according to claim 1, further comprising:

a resistance channel portion having a channel cross-sectional area that is 1/10 or less of a channel cross-sectional area of a communication-channel in a part of the communication-channels in order to adjust flow rates.

9. A cell culture method, comprising:

preparing the cell culture apparatus according to claim 1, a first step of opening a lid of the connected culture container and seeding and adhering cells in each of the culture chambers in the cell culture apparatus;

a second step of filling first row-culture chambers in the first direction with a liquid culture medium and closing the lid in the cell culture apparatus where the first row-culture chambers are disposed on a same row along the second direction;

a third step of pressurizing an inside of the first row-culture chambers and opening second row-culture chambers in the first direction which are disposed on a same row along the second direction to atmospheric pressure, thereby sending the liquid culture medium to the second row-culture chambers from the first row-culture chambers through the communication-channels;

a fourth step of sequentially pressurizing the culture chambers and opening the culture chambers to atmospheric pressure in ascending order of row numbers in the first direction, thereby sending the liquid culture medium from the m-1$^{th}$ row-culture chambers in the first direction to the m$^{th}$ row-culture chambers through the communication-channels;

a fifth step of pressurizing an inside of the m$^{th}$ row-culture chambers and opening an inside of the first row-culture chambers to atmospheric pressure, thereby sending the liquid culture medium from the m$^{th}$ row-culture chambers to the first row-culture chambers through the communication-channels; and a sixth step of repeating the third step through the fifth step, thereby circulating the liquid culture medium in each of the culture chambers in the cell culture apparatus.

* * * * *